US012287438B2

(12) United States Patent
Palm et al.

(10) Patent No.: US 12,287,438 B2
(45) Date of Patent: Apr. 29, 2025

(54) ION BEAM EMISSION APPARATUS AND DETECTION SYSTEM THEREFOR

(71) Applicant: TERAPET SA, Satigny (CH)

(72) Inventors: Marcus Palm, Arzier-le Muids (CH); Christina Vallgren, Arzier-le Muids (CH)

(73) Assignee: TERAPET SA, Satigny (CH)

( * ) Notice: Subject to any disclaimer, the term of this patent is extended or adjusted under 35 U.S.C. 154(b) by 168 days.

(21) Appl. No.: 17/791,463

(22) PCT Filed: Jan. 9, 2021

(86) PCT No.: PCT/EP2021/050319
§ 371 (c)(1),
(2) Date: Jul. 7, 2022

(87) PCT Pub. No.: WO2021/140233
PCT Pub. Date: Jul. 15, 2021

(65) Prior Publication Data
US 2023/0041293 A1 Feb. 9, 2023

(30) Foreign Application Priority Data

Jan. 10, 2020 (EP) .................. 20151273.8

(51) Int. Cl.
*G01T 1/20* (2006.01)
*A61B 6/03* (2006.01)
*A61B 6/42* (2024.01)
(52) U.S. Cl.
CPC .......... *G01T 1/20181* (2020.05); *A61B 6/037* (2013.01); *A61B 6/4258* (2013.01)
(58) Field of Classification Search
CPC .... A61B 6/037; A61B 6/4258; G01T 1/20181
See application file for complete search history.

(56) References Cited

U.S. PATENT DOCUMENTS 4,749,863 A * 6/1988 Casey .................... G01T 1/202
250/363.04
5,464,984 A 11/1995 Cox et al.
(Continued)

FOREIGN PATENT DOCUMENTS

| CN | 107544086 | 1/2018 |
| EP | 1 617 237 | 1/2006 |

(Continued)

OTHER PUBLICATIONS

Doroud, K., et al., "The Strip Silicon Photo-Multiplier: An innovation for enhanced time and position measurement", Nuclear Instruments and Methods in Physics Research A, vol. 853, 2017, 8 pages.

(Continued)

*Primary Examiner* — Blake C Riddick
(74) *Attorney, Agent, or Firm* — Nixon & Vanderhye PC

(57) ABSTRACT

Gamma ray detection system comprising a detection module assembly including at least two detection modules configured for positron emission tomography (PET) scanning of a target zone, each detection module comprising a plurality of stacked scintillator plates each having a major surface oriented to generally face the target zone and lateral minor surfaces defining edges of the scintillator plates, a plurality of photon sensors being mounted against said edges layer photon sensor 18a configured to detect a scintillation event in the scintillator plate from a gamma ray incident on the major surface. The gamma ray detection system is further configured to function as a Compton camera, at least one scintillator plate that is not the scintillator plate closest to the target zone being configured as an absorber scintillator plate for said Compton camera.

3 Claims, 25 Drawing Sheets

(56) References Cited

U.S. PATENT DOCUMENTS

| | | | | |
|---|---|---|---|---|
| 5,525,803 | A * | 6/1996 | Watanabe | G01T 1/1642 250/369 |
| 5,821,541 | A * | 10/1998 | Tumer | G01T 1/2928 250/363.03 |
| 6,194,728 | B1 * | 2/2001 | Bosnjakovic | G01T 1/2985 250/369 |
| 8,084,742 | B1 * | 12/2011 | Nagarkar | G01T 1/2008 250/363.03 |
| 8,405,035 | B1 * | 3/2013 | Nagarkar | G01T 1/2008 250/361 R |
| 2002/0008205 | A1 | 1/2002 | Kurfess et al. | |
| 2004/0159792 | A1 * | 8/2004 | Andreaco | G01T 1/1648 250/363.03 |
| 2005/0094763 | A1 | 5/2005 | Sherman et al. | |
| 2005/0116173 | A1 | 6/2005 | Hristov et al. | |
| 2005/0253073 | A1 * | 11/2005 | Joram | G01T 1/2985 250/366 |
| 2006/0192128 | A1 * | 8/2006 | Benlloch Bavciera | G01T 1/1642 250/369 |
| 2006/0202125 | A1 * | 9/2006 | Suhami | G01T 1/202 250/368 |
| 2007/0221858 | A1 | 9/2007 | Abenaim et al. | |
| 2007/0253530 | A1 * | 11/2007 | Mihailescu | A61B 6/037 378/22 |
| 2008/0230704 | A1 * | 9/2008 | Daghighian | A61B 8/5238 250/363.02 |
| 2010/0090117 | A1 * | 4/2010 | Nelson | G01T 1/2002 250/363.04 |
| 2010/0096555 | A1 * | 4/2010 | Nelson | G01T 1/202 250/361 R |
| 2010/0187424 | A1 * | 7/2010 | Majewski | G01T 1/1603 250/363.05 |
| 2010/0219346 | A1 * | 9/2010 | Daghighian | A61B 17/3403 250/363.03 |
| 2010/0270462 | A1 * | 10/2010 | Nelson | G01T 1/20181 250/252.1 |
| 2012/0112079 | A1 * | 5/2012 | Moskal | A61B 6/037 250/361 R |
| 2013/0009067 | A1 * | 1/2013 | Schmand | G01T 1/1642 250/366 |
| 2013/0279658 | A1 * | 10/2013 | Mazin | A61B 6/54 378/62 |
| 2015/0098640 | A1 * | 4/2015 | Berker | A61B 6/5258 382/131 |
| 2015/0192685 | A1 * | 7/2015 | Griesmer | G01T 1/1647 250/362 |
| 2015/0331115 | A1 * | 11/2015 | Nelson | G01T 1/1614 250/366 |
| 2015/0331118 | A1 * | 11/2015 | Iltis | G01T 1/208 250/362 |
| 2016/0131774 | A1 * | 5/2016 | Lage | A61B 6/5217 600/425 |
| 2017/0123084 | A1 * | 5/2017 | Ferenc | G01T 1/20188 |
| 2018/0136340 | A1 * | 5/2018 | Nelson | G01T 1/1611 |
| 2018/0136344 | A1 * | 5/2018 | Nelson | G01T 1/20181 |
| 2018/0172847 | A1 | 6/2018 | Nelson et al. | |
| 2018/0172849 | A1 * | 6/2018 | Nelson | G01T 1/20182 |
| 2018/0217276 | A1 * | 8/2018 | Iltis | G01T 1/1642 |
| 2018/0252825 | A1 * | 9/2018 | Benlloch Baviera | G01T 1/208 |
| 2019/0107637 | A1 * | 4/2019 | Nelson | G01T 1/242 |
| 2019/0187302 | A1 * | 6/2019 | Nelson | G01N 23/046 |
| 2019/0317227 | A1 * | 10/2019 | Nelson | A61B 6/032 |
| 2019/0353807 | A1 * | 11/2019 | Furenlid | G01T 1/20185 |
| 2021/0007682 | A1 * | 1/2021 | Chmeissani Raad | A61B 6/4266 |
| 2021/0199821 | A1 * | 7/2021 | Iltis | G01T 1/2907 |

FOREIGN PATENT DOCUMENTS

| | | |
|---|---|---|
| JP | 2011-149883 A | 8/2011 |
| WO | 2004/008177 | 1/2004 |
| WO | 2014/209972 | 12/2014 |
| WO | 2018/081404 | 5/2018 |

OTHER PUBLICATIONS

Jan, Meei-Ling, et al., "Use of a LYSO-based Compton camera for prompt gamma range verification in proton therapy", Medical Physics, vol. 44, No. 12, Dec. 2017, pp. 6261-6269.

Knopf, Antje-Christin, et al., "In vivo proton range verification: a review", Physics in Medicine and Biology, vol. 58, 2013, pp. R131-R160.

Rohling, H., et al., "Requirements for a Compton camera for in-vivo range verification of proton therapy", Physics in Medicine and Biology, 2017, 21 pages.

International Search Report and Written Opinion of the International Searching Authority dated Jul. 28, 2021, for PCT/EP2021/050319, 25 pp.

Kenji Shimazoe et al., "Development of simultaneous PET and Compton imaging using GAGG-SiPM based pixel detectors", Nuclear Instruments and Methods in Physics Research, Section A, Elsevier BV, vol. 954, No. 9, Nov. 9, 2018, 6 pp.

D F C Hsu et al., "Intercrystal scatter studies for a 1mm3 resolution clinical PET system prototype", Physics in Medicine & Biology, vol. 64, No. 9, May 2, 2019, 12 pp.

Gregory Shakirin et al., "Implementation and workflow for PET monitoring of therapeutic ion irradiation: a comparison of in-beam, in-room, and off-line techniques", Physics in Medicine and Biology, vol. 56, 2011, pp. 1281-1299 (19 pp.).

Notice of Reasons for Refusal issued on Jan. 14, 2025 in corresponding Japanese Application No. 2022-542415 (English-Language Translation), 2 pages.

* cited by examiner

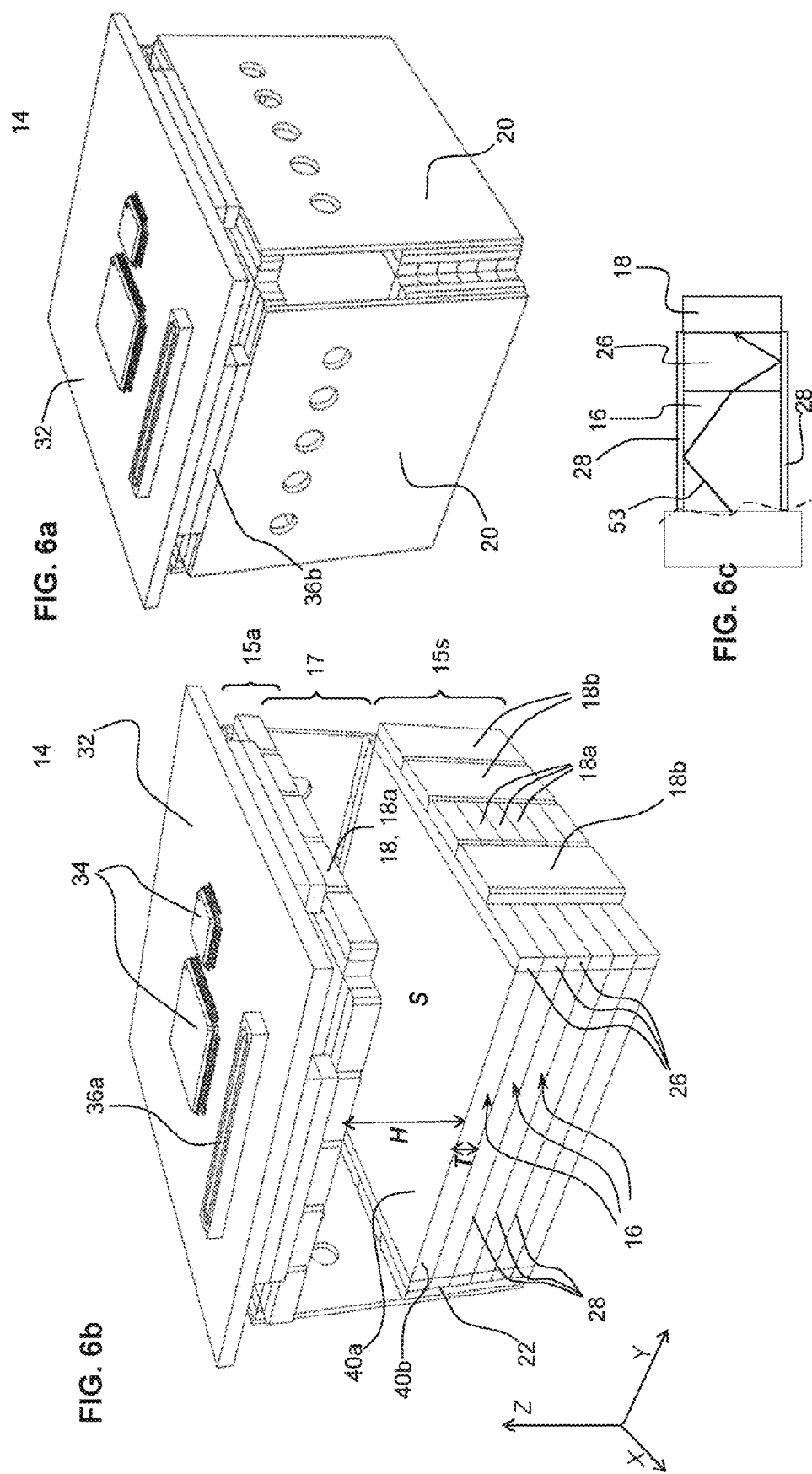

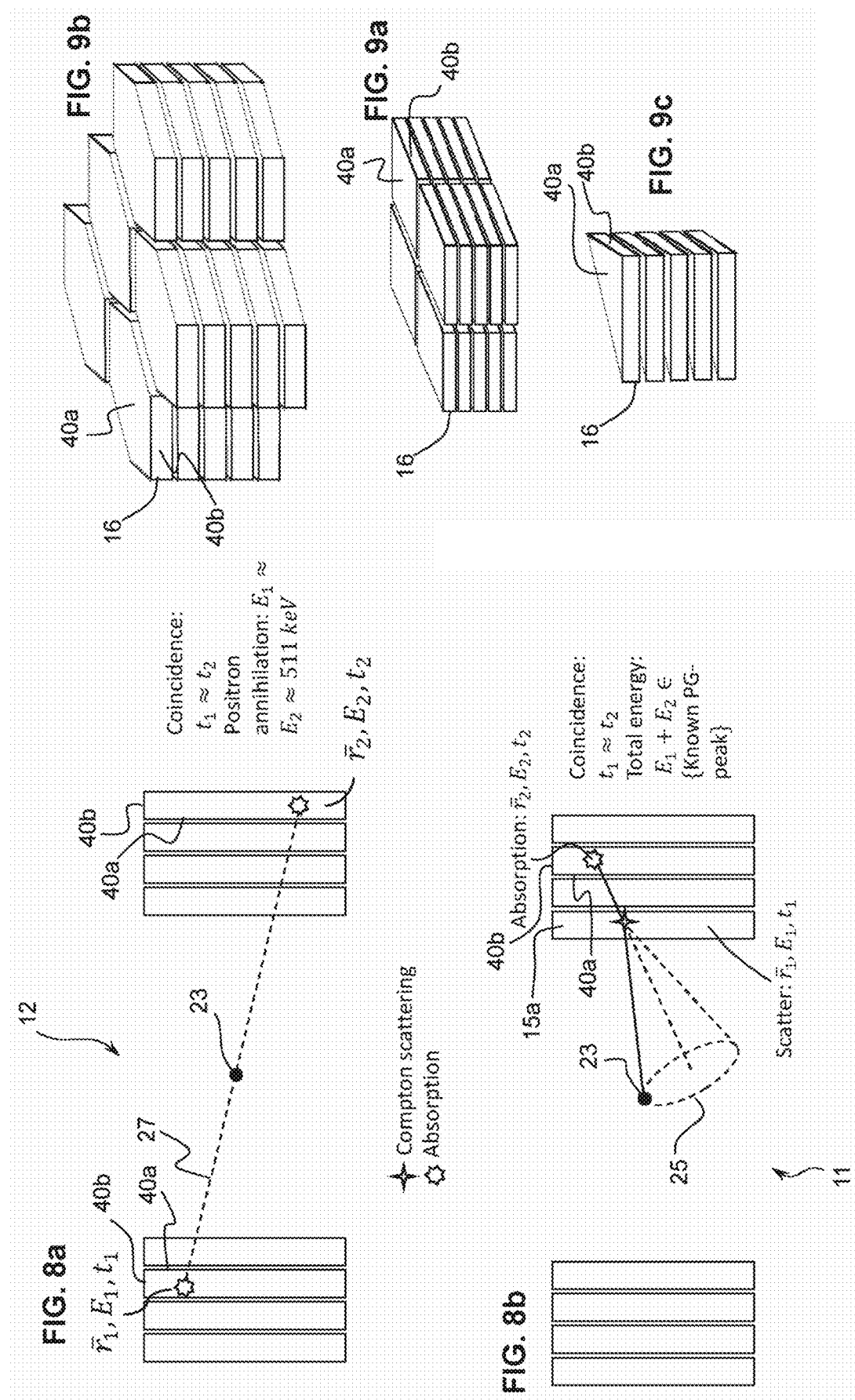

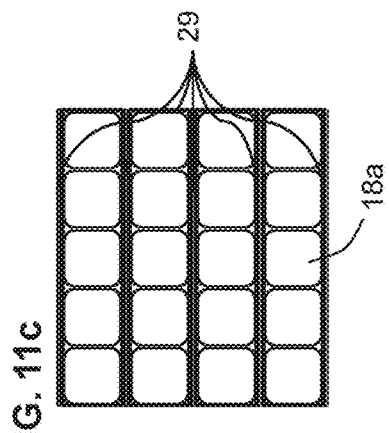
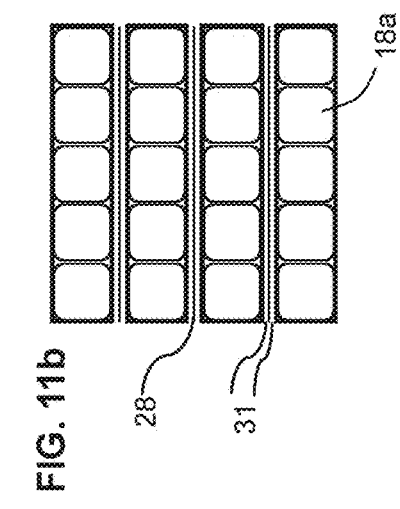
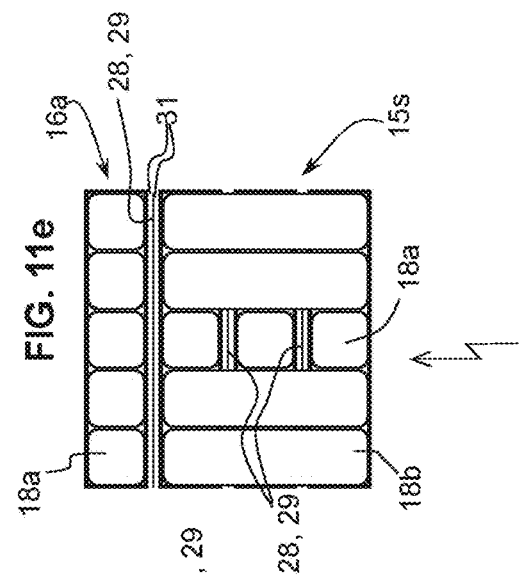
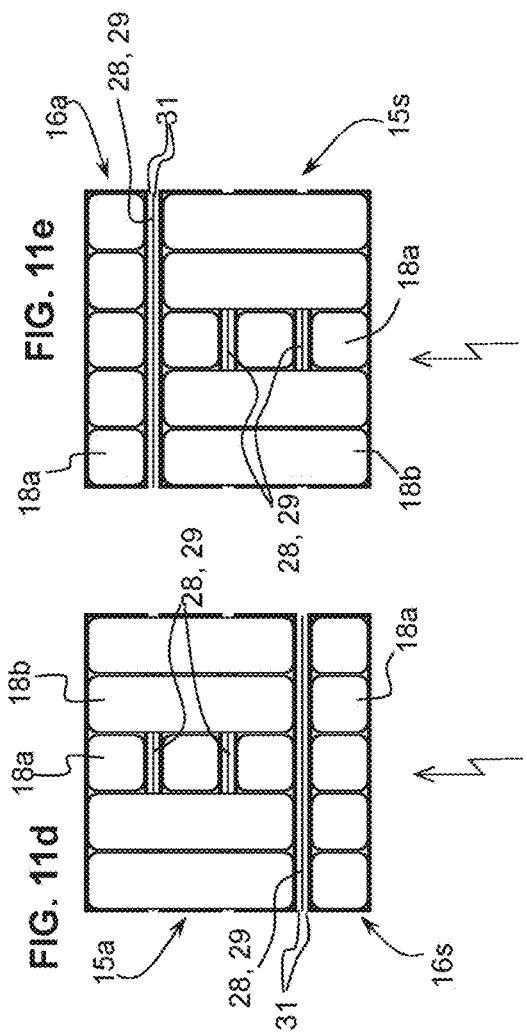
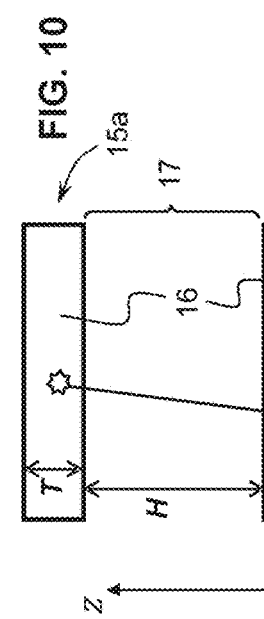
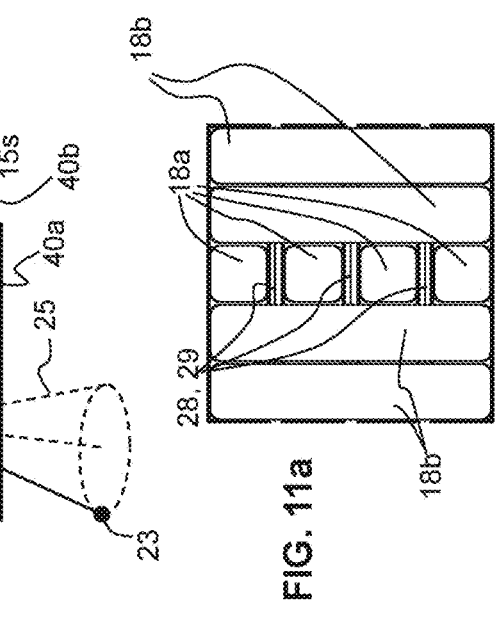

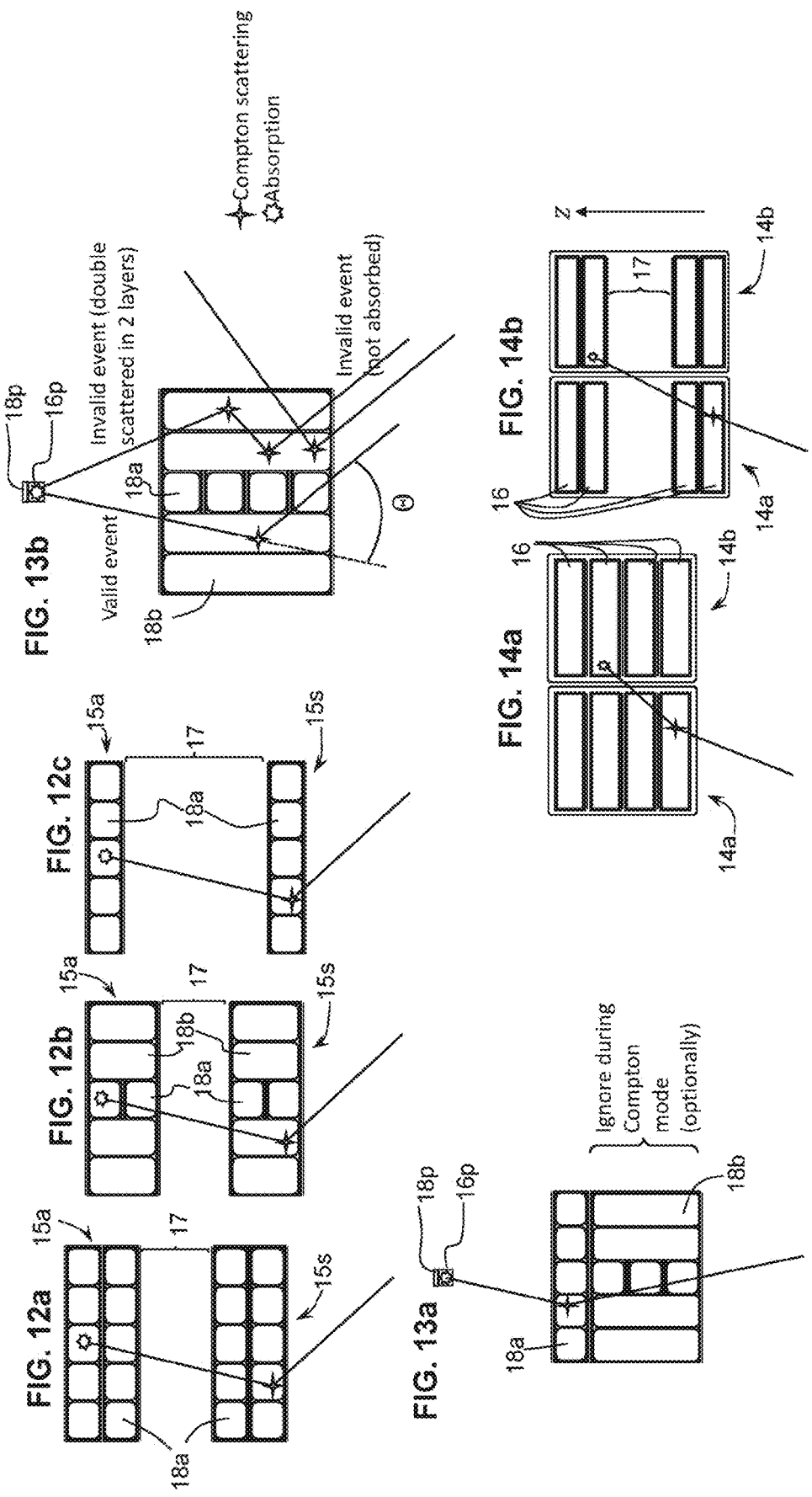

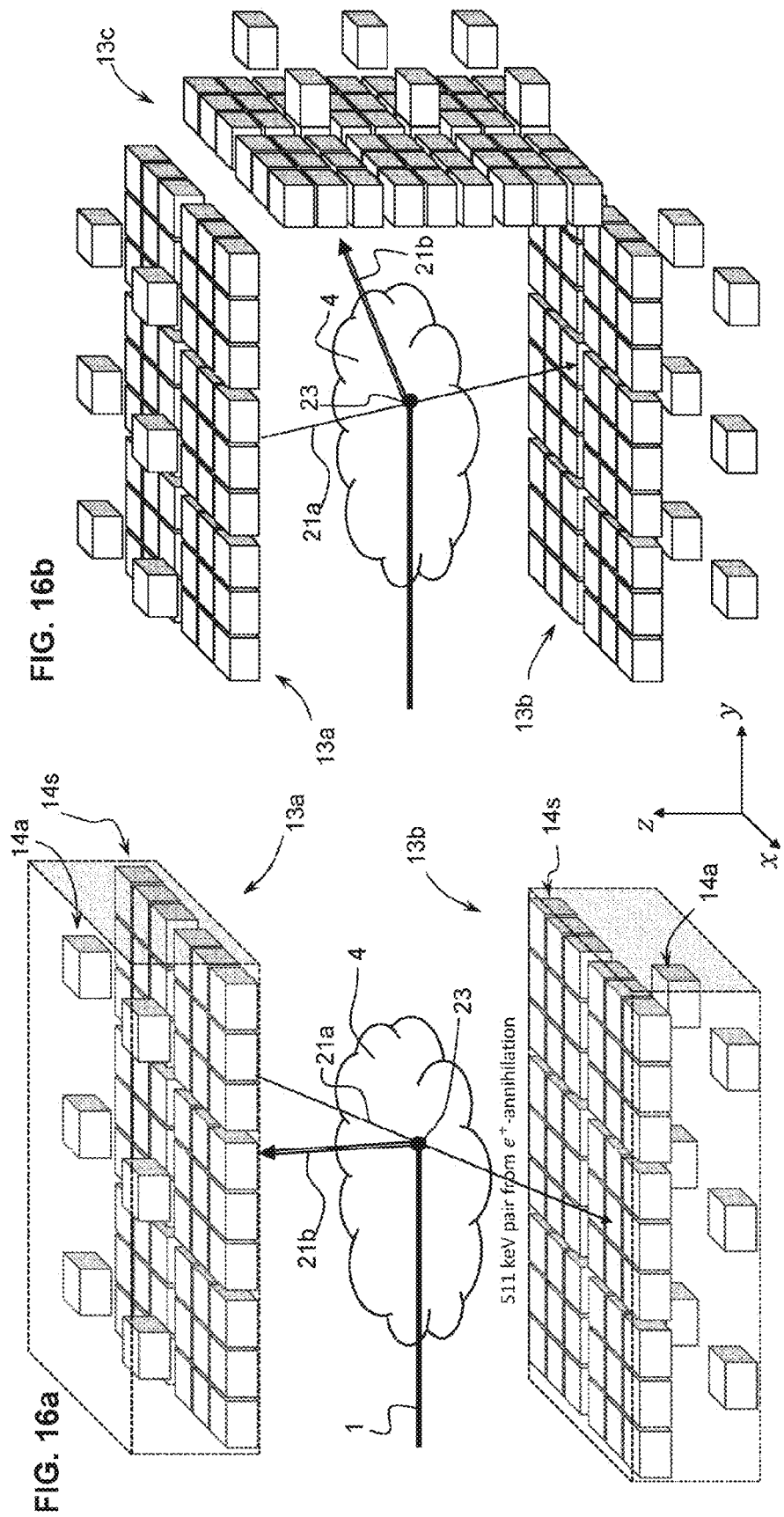

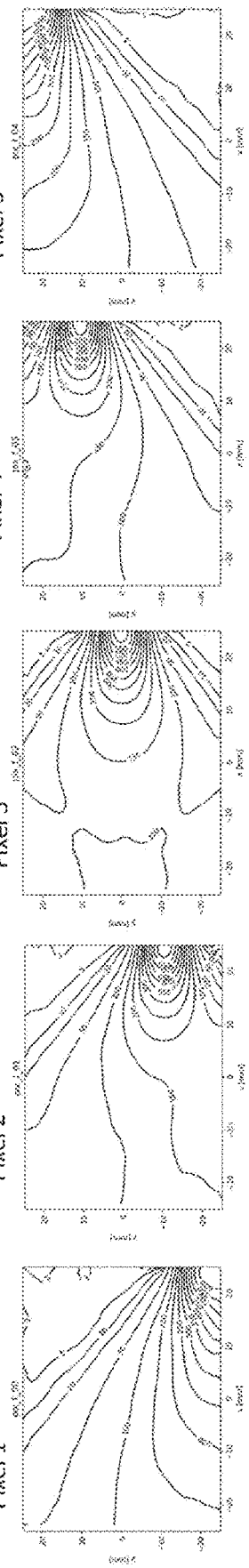
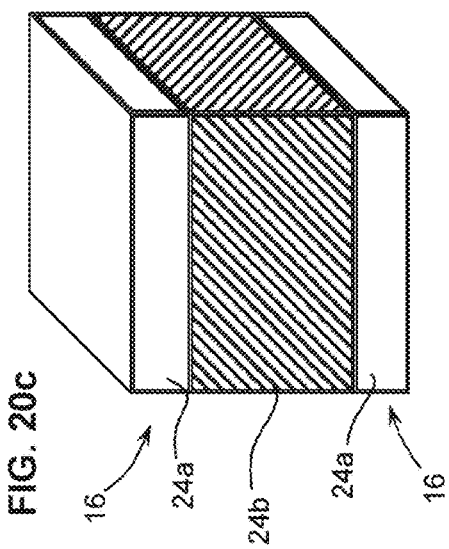
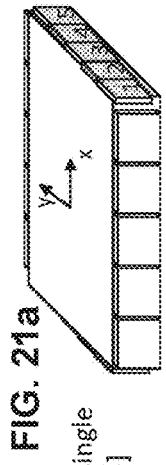
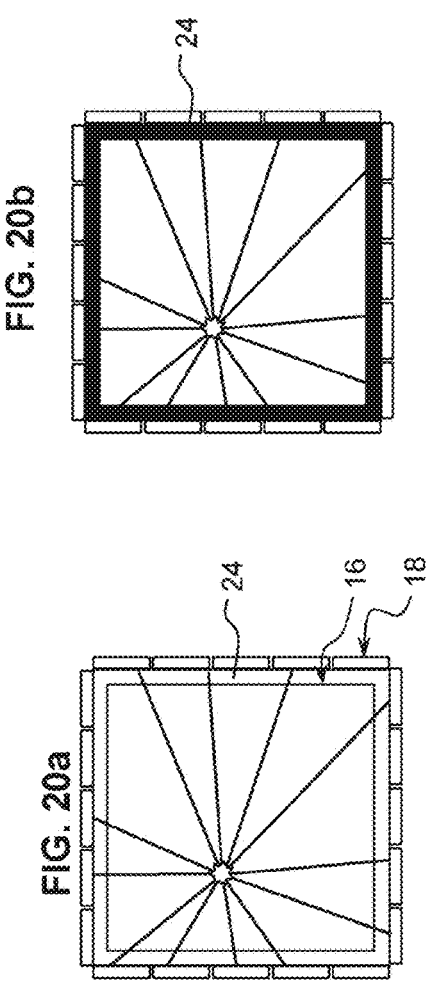
FIG. 20a
FIG. 20b
FIG. 20c
FIG. 21a
FIG. 21b
[Mean number of photons detected by a single photon detector along right edge, $\mu_i(x, y)$]

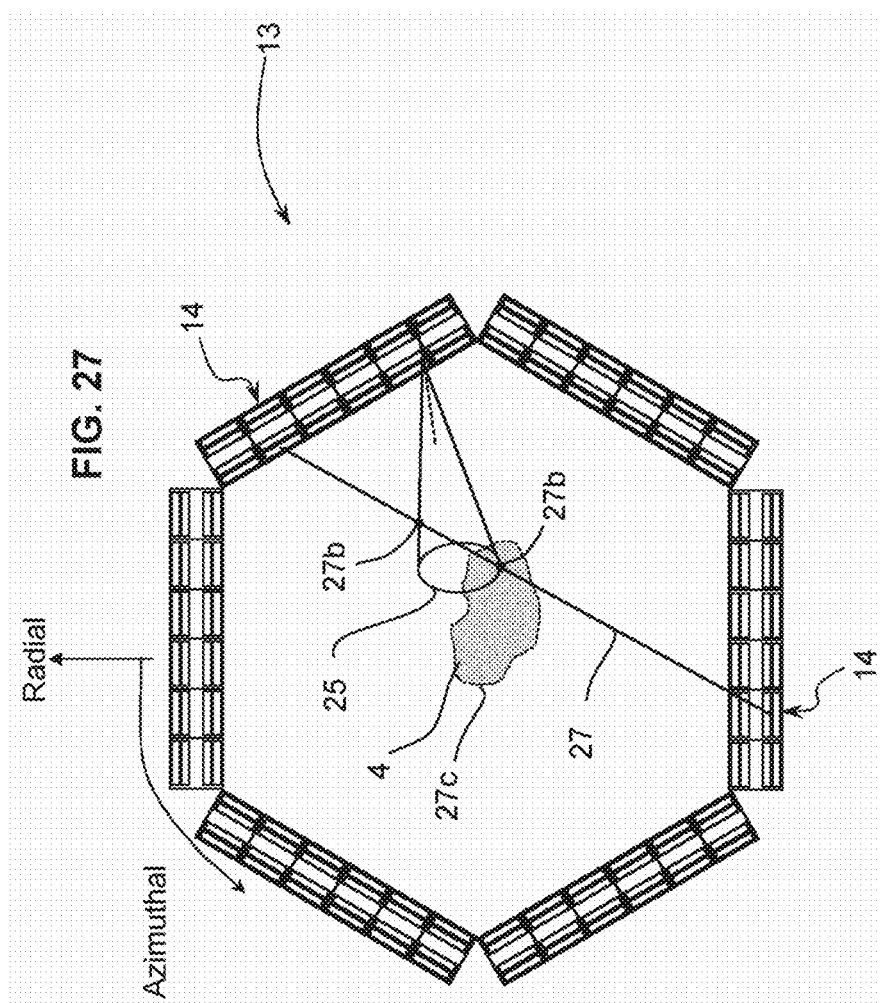

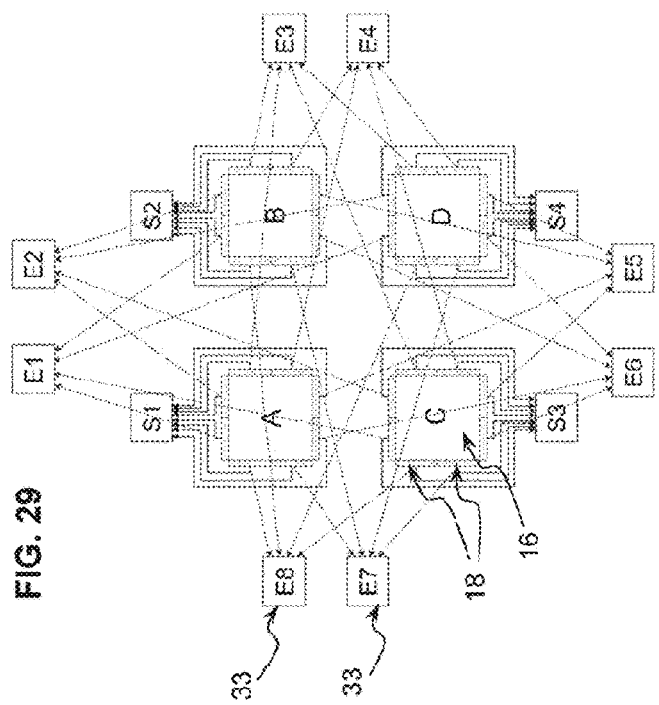
FIG. 29
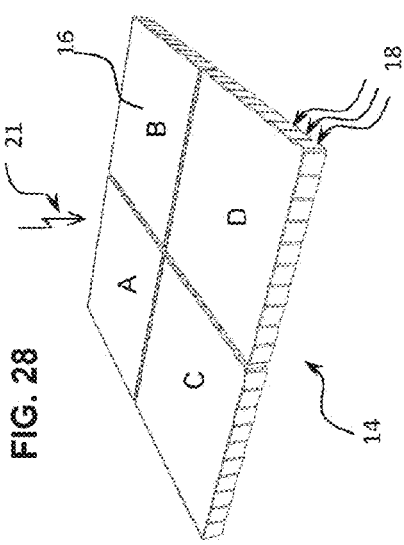
FIG. 28
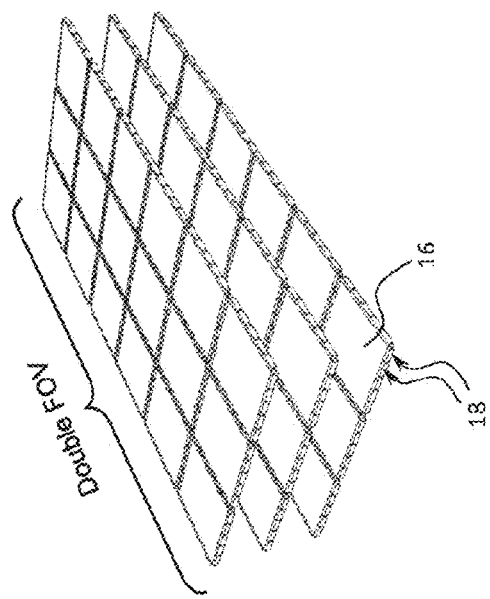
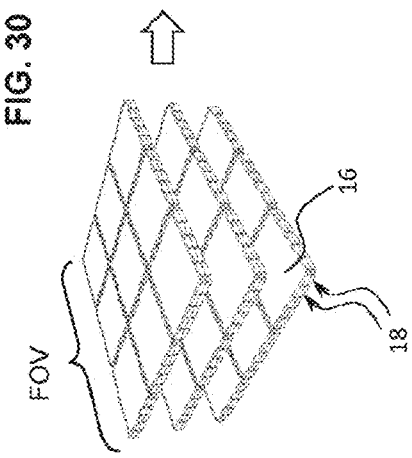
FIG. 30

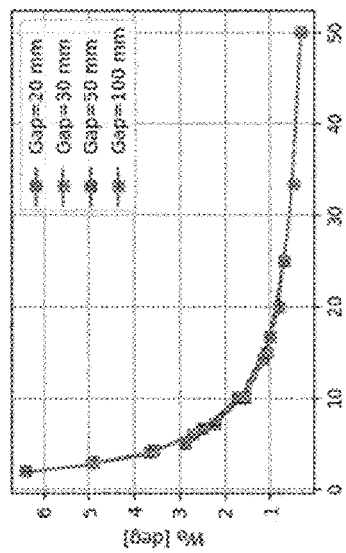

FIG. 35

Angular precision for different gap and layer thickness combinations.
Horizontal axis: ratio Gap/Layer thickness (H/T)
Vertical axis: Angular spread due to coordinate error, in degrees

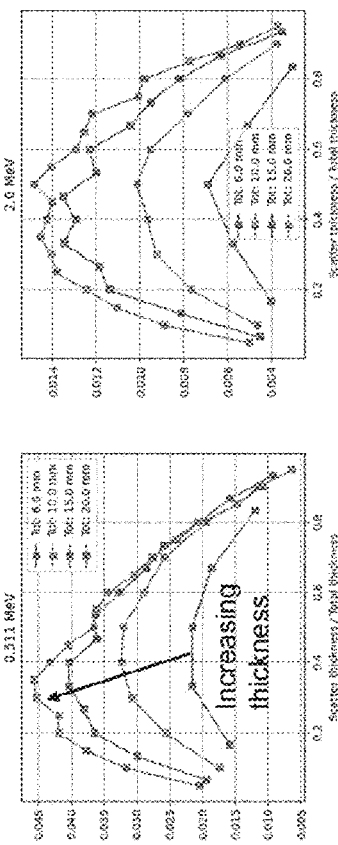

FIG. 34

Probabilities of valid 2-stage Compton events (Compton scattering followed by photoelectric absorption) in a 2-layer module vs. ratio between inner scintillator thickness and outer scintillator thickness, for gamma energies between 0.511 to 7 MeV and total scintillator thickness from 6 to 20 mm.

ION BEAM EMISSION APPARATUS AND DETECTION SYSTEM THEREFOR

This application is the U.S. national phase of International Application No. PCT/EP2021/050319 filed Jan. 9, 2021, which designated the U.S. and claims priority to EP 20151273.8 filed Jan. 10, 2020, the entire contents of each of which are hereby incorporated by reference.

TECHNICAL FIELD

The present invention relates to an ion beam emission apparatus, and a detection system therefor. The ion beam emission apparatus may in particular relate to a medical apparatus, for ion beam therapy, for instance for proton beam irradiation of tumors. The detection system is for detecting gamma rays. The detection system may be used for dose and range monitoring during ion beam therapy treatment. The use of the detection system is not only limited to irradiation therapy for human beings or animals, but can also be used as conventional PET-scanner or Compton camera for other uses.

BACKGROUND

Proton or heavy ion/Ion beam therapy is one of the most precise methods of external radiation therapy. Unlike a photon beam which has a high entrance dose and decreases gradually while passing through the body, an ion can penetrate through tissues and deposit most of its energy near the end of its track, known as the Bragg peak. In the present text, reference to the term "ion" in a general sense should also be understood to encompass negatively charged or positively charged ions, including protons.

In today's state-of-the-art ion beam systems for radiation therapy, as illustrated in FIG. 1, the dose of irradiation is typically delivered by a narrow, typically a few mm, ion beam 1 of a defined energy that is directed toward the patient and transversally deflected using fast ramped scanning magnets 2. The penetration depth of the beam is controlled by modulating the energy of the beam and its intensity and transverse position and size before reaching the target area is registered by beam intensity and profile monitors 3. In this manner, the tumor is irradiated in 3D (three dimensions). The target area may be divided into iso-energy slices 4, corresponding to the penetration depths of a given set of beam energies. Each iso-energy slice is divided into a sequence of "spots" with different transverse coordinates, where each spot shall receive a certain number of particles.

In practice, ion beam therapy usually requires the establishment of a treatment plan (as illustrated in FIG. 2) before any treatment can start. During this treatment plan, a computer tomography scan (CT scan), possibly combined with MRI (Magnetic Resonance Imaging) and/or PET (Positron Emission Tomography) scan of the patient and target tissues is generally performed. The CT/MRI/PET scans are used to delineate the target volume and define the desired dose distribution. Then, one calculates how the protons should be delivered: from which entrance angles the proton beam should enter, which beam energies to use to position the Bragg Peak at the desired locations, the shape and size of the beam before entering the patient and the number of protons to be delivered per "spot", as illustrated in FIG. 1.

The process is normally performed several days or weeks before the actual treatment starts (indicated at time of t0 in FIG. 2) and treatment of a single patient may take several weeks distributed over several treatment sessions. During this time period, the position and volume of the target tissue can significantly change. To verify the validity of the treatment plan, the patient is often imaged right before each treatment session, which makes it possible to ensure that the patient position (with respect to the table and imaging device) is correct. Anatomical changes that may have an impact on the dose distribution may also be detected. Apart from patient positioning and changes in patient anatomy, there are a range of other factors that may cause a discrepancy between the planned and delivered dose distribution in general, and beam range in particular, as illustrated in FIG. 2. There may be imaging artefacts, in particular for patients with metal implants—not uncommon for patients who have previously undergone surgery.

The tissue model generated from the images may suffer from systematic errors, as well as the conversion from CT-images to proton range. Tissue heterogeneities along the beam path, from skin to target may introduce large uncertainties in beam range calculations. The patient setup or immobilization may vary from treatment session to treatment session. During irradiation, organ motion, which may be caused by respiratory motion, heartbeat, peristalsis or slower drift due to the patient changing position from standing to supine or prone, may also displace the Bragg peak from the desired position. Of particular concern is the situation where the tumour is close to a critical organ: spine, optical nerve, brain stem, etc. Due to the steep gradient of dose fall-off at the Bragg peak region, range deviations in ion therapy have more severe consequences than in photon therapy. A range error could mean a portion of a tumour not receiving any radiation dose at all (under-shooting), or the normal tissue lying distal to the beam receiving a high dose (over-shooting).

While passing through tissue, protons/heavy ions undergo nuclear reactions, some of which result in the emission of gamma rays. There are two types of gamma rays that can be detected for treatment monitoring: 1) Coincident gamma rays from the production of positron emission isotopes. 2) Prompt gamma rays from excitations of the target nuclei. The first type may be detected using positron emission tomography (PET) scanning which is widely used today. It has broad applications in neurology and oncology due to its ability to monitor metabolism of glucose and the uptake of other targeting radiotracers in specific organs and tissues. One particular use case for PET scanning is in ion beam therapy, where the penetration depth of the beam in the patient can be uncertain due to tissue heterogeneities, and safety margins must be employed to spare critical organs from dose and/or ensuring sufficient dose is given to the entire tumour. A PET scan can give information on exactly where in the patient an irradiation dose has been deposited. However, there are many practical and technical issues with using conventional PET scanners under ion beam therapy treatments.

Examples of conventional PET-scanning used in the clinical workflow are as follows (Shakirin 2011):

Off-line PET. The PET-scan is made after irradiation, often with a delay of several minutes when the patient is transported from the irradiation room to another room housing the PET-scanner. Only isotopes with lifetimes in the order of minutes can be detected. Although off-line PET can be carried out with conventional PET-scanners, the relatively long delay for PET acquisitions, depending on the distance between the treatment and imaging room, does not allow acquisition of emissions from short-lived radionuclide species. Off-line PET can measure only long half-life contributions. Performance is further degraded by biological washout of the proton induced PET activity, which reduces the activity level in the target region, resulting in a "blurred" image.

In-room PET. The PET-scan takes place shortly after irradiation, using a PET scanner located in the treatment room. Although the delay between irradiation and scanning is reduced compared to off-line systems, there is still some delay. Furthermore, this approach prolongs the occupation time of the irradiation room, effectively reducing overall patient throughput.

In-beam PET: measurement of positron annihilation activity during irradiation by means of a customized PET scanner integrated into the treatment site or directly into the gantry. The real-time data acquisition allows for more accurate dose and range control. The PET activity level in the tissue is at the highest level for both long half-life ($^{11}$C, $^{13}$N, etc) and short half-life ($^{15}$O, $^{10}$C, etc) components and the effect of biological washout is minimal. However, integration of a dedicated PET system into the beam delivery system for real-time measurement is expensive and technically demanding due to the geometric constraints of integration in the ion beam apparatus in a treatment environment, and the intensive computation of real-time measurement based on the large number of signals output by the gamma ray detectors. Moreover the performance of in-beam PET devices is limited due inter alia to the drowning of coincidence events by prompt gamma emissions during ion beam delivery and the delay in positron annihilation with respect to irradiation (stochastic emission according to the lifetime of produced isotopes). Nevertheless, PET scanning technology and image reconstruction methods are mature and proven and are also advantageous in allowing image acquisition to continue after ion beam emission, even when the patient is outside the room. Imaging quality can be improved by increasing imaging acquisition time, even after irradiation is finished. Likewise, idle time between portals could be used for imaging. A further important advantage of PET scanning is that it allows total dose measurement.

In WO 2018/081404 A1 a PET scanner scintillation detector with edge-detection and the possibility of radially stacking several sensor blocks to achieve inherent depth-of-interaction resolution is disclosed. The edge detection disclosed therein reduces the number of scintillator elements, compared to a conventional pixelated scintillator arrangement while at the same time improving depth of interaction measurement. However, with multiple scintillator plates, the number of photon sensors remains high and the associated signal processing requirements for real-time acquisition would be demanding.

Another per se known technique to verify the proton beam range is via the measurement of prompt gamma ray (PG) emission (Knopf 2013). PG emission is substantially simultaneous with proton beam emission and there is therefore essentially no delay between the emission and detection during treatment. Spot-by-spot imaging is also possible as is imaging closer to the particle end-range. PG detection thus allows rapid detection of significant range deviations. PG detection is however an immature technology and image reconstruction is rather complicated whereby image quality cannot be improved by increasing imaging time, the detector performance and gamma absorption efficiency being key factors for image quality. Moreover, total dose reconstruction is difficult.

CN 107544086 A [1] discloses a combined Compton-PET imaging apparatus, based on scintillators. The gamma ray detection elements are of type face-on ("top-on") or edge-on ("side-on"), as illustrated in FIG. 39. Compton scattering between radially separated detection modules 50 allows for Compton camera imaging, while coincident photoelectric absorption allows for PET-scanning. Detection probes containing multiple scintillation crystal arrays 51, separated by radial gaps, are disclosed. However, the radial gaps are occluded by either photon sensor arrays 52 or light guides (e.g. optical fibres). The major surface (generally facing the imaging volume) of each scintillation crystal array is thus covered with photon sensors. CN 107544086 A does not disclose, however, how or if the desired Compton scattering angular precision is achieved.

Shimazoe 2018 [3] discloses a similar setup, with 2D face-coupled scintillator arrays 50 (GAGG:Ce) coupled to 2D arrays of photon sensors 52.

SUMMARY OF THE INVENTION

A general object of the invention is to provide a safe, reliable and accurate ion beam emission apparatus.

A specific object of the invention in the medical field is to provide a safe, reliable and accurate ion beam emission apparatus for irradiation therapy of patients.

Another object of the invention is to provide a cost effective detection system allowing accurate real-time imaging of a volume of interest (also referred to herein as "target zone") emitting positron and prompt gamma rays.

Another object of the invention is to provide a cost effective detection system for integration in an ion beam emission apparatus for safe, reliable, and accurate real-time control of ion beam emission.

A specific object of the invention in the medical field is to provide a cost effective detection system for safe, reliable, and accurate real-time control of ion beam emission therapy.

Disclosed herein, according to an aspect of the invention, is a gamma ray detection system comprising a detection module assembly including at least two detection modules configured for positron emission tomography (PET) scanning of a target zone, each detection module comprising a plurality of stacked monolithic scintillator plates each having a major surface oriented to generally face the target zone and lateral minor surfaces defining edges of the scintillator plates, the major surface having a greater surface area than the surface area of the lateral minor surfaces, and a plurality of photon sensors being mounted against each of said edges configured to detect and determine the position within the plane of the major surface of scintillation events in the scintillator plates from gamma rays incident on the major surfaces. The gamma ray detection system is further configured to function as a Compton camera, at least one scintillator plate that is not the scintillator plate closest to the target zone being configured as an absorber scintillator plate for said Compton camera.

Also disclosed herein is an ion beam therapy system for ion beam irradiation of a zone of tissue, comprising a patient support and an ion beam emitter relatively movable about at least an axis of rotation, and said gamma ray detection system configured for prompt gamma ray detection and PET scanning during, between and after ion beam irradiation.

In an advantageous embodiment, a plurality of photon sensors of at least two radially stacked scintillator plates are connected to a processing circuit configured to multiplex a readout of said plurality of photon sensors.

In an advantageous embodiment, a plurality of photon sensors of at least two azimuthally-axially arranged scintillator plates are connected to a processing circuit configured to multiplex a readout of said plurality of photon sensors.

In an advantageous embodiment, at least one radial gap is provided between at least two of said plurality of stacked scintillator plates or between at least two detection modules.

In an advantageous embodiment, the height H of the radial gap in relation to the thickness T of one of said plurality of scintillator plates may typically be in the range of 200>H/T>2, preferably in a range of 50>H/T>10.

In an advantageous embodiment, said plurality of photon sensors include at least one strip multilayer photon sensor extending over edges of a plurality of layers.

In an advantageous embodiment, a plurality of said strip multilayer photon sensors are mounted on each edge side of said plurality of stacked scintillator plates.

In an advantageous embodiment, said at least one strip multilayer photon sensor is a dual-end strip detector configured for measuring the arrival time of the signal at both ends.

In an advantageous embodiment, said plurality of photon sensors includes at least one individual layer photon sensor on at least one edge of each scintillator plate. In a preferred embodiment, especially for scintillator plates having four or more edges (e.g. square or hexagonal scintillator plates), there are individual layer photon sensors on two edges, or more than two edges, of each scintillator plate.

In an advantageous embodiment, said individual layer photon sensors of an assembly of sensor plates, each sensor plate comprising a scintillator plate and associated photon sensors, are interconnected in a cross-wire connection or resistive network arrangement such that the readout is a sum and/or a weighted sum of the signals of a plurality of interconnected individual layer photon sensors.

In an advantageous embodiment, said individual layer photon sensors of a module are multiplexed such that the number of readout signals is a subset of the total number of module photon sensors.

In an advantageous embodiment, the detection system further comprises a light reflective or light absorbing interface layer between, or on, at least two of said scintillator plates.

In an advantageous embodiment, the detection system further comprises a low refractive index gap, for instance of air, between at least two of said scintillator plates.

In an advantageous embodiment, the detection system further comprises an electro-optical shutter between the edges of at least one scintillator plate and the photon sensors.

In an advantageous embodiment, the electro-optical shutter comprises a light spreader material and thickness configured to spread light from a scintillation event close to the edge.

In an advantageous embodiment, a surface area S of the major surface of the scintillator plate and a thickness T of the scintillator plate lie in ranges 100 mm$^2$<=S<=40000 mm$^2$, and 0.5 mm<=T<=30 mm.

In an advantageous embodiment, the detection module assembly surrounds a target zone and comprises at least one gap or orifice for ion beam emission therethrough.

In an advantageous embodiment, the photon sensors that are optically edge-coupled to one or several sides of the stack of scintillator plate, are mounted on support boards comprising edge connectors for coupling to the signal processing circuit board, the edge connectors minimizing the gap between adjacent detection modules of the detection module assembly.

In an advantageous embodiment, said radial gap satisfies the relationship H/(T1+T2)>5, where T1 and T2 are the thicknesses of the two scintillators surrounding the radial gap and H is the height of the radial gap.

In an advantageous embodiment, a total thickness of the plurality of stacked monolithic scintillator plates in the radial direction is less than 19 mm.

In an advantageous embodiment, the gamma ray detection system comprises two radially stacked scintillator plates having a ratio between a thickness of the radially inner scintillator plate and the total radial scintillator thickness in the range 0.2 to 0.6.

In an advantageous embodiment, the photon sensor bias voltage of photon sensors of individual scintillator plates may be independently adjusted or enabled/disabled.

In an advantageous embodiment, photon sensors coupled to at least two radially stacked scintillator plates are connected to processing circuitry configured to apply Compton kinematic rules to determine whether two coincident block events corresponds to a forward- or backward-scattered Compton scattering followed by absorption.

In an advantageous embodiment, the processing circuitry is configured to reject events appearing to originate from primary gamma rays entering the detector from a radially outward direction.

In an advantageous embodiment, the processing circuitry is configure to utilize the interaction coordinates of the photoelectric absorption as LOR-end point for a small-angle, forward-Compton scattered gamma ray originating from electron-positron annihilation.

In an advantageous embodiment, the processing circuitry is configured to discard Compton scattered events exceeding a configurable, primary gamma ray energy-dependent, scattering angle in order to improve angular resolution.

In an advantageous embodiment, analog signals from adjacent photon sensors are added prior to digitization or other multiplexing circuits.

In an advantageous embodiment, a two-stage Compton camera may be implemented via inter-module scattering between adjacent detection modules of the detection module assembly.

In an advantageous embodiment, a two-stage Compton camera may be implemented via inter-block scattering between adjacent sensor plates.

In an advantageous embodiment, a three-stage Compton camera may be implemented via inter-block scattering between adjacent sensor plates.

Advantageous features of the invention compared to conventional PET-scanners, are substantially higher spatial resolution and low-cost scalability. The latter is important in order to reach a high sensitivity, which is particularly important in the medical field, in particular for range and dose verification for proton therapy. According to an advantageous aspect of the invention, the combined PET-scanner/Compton camera enables exploitation of the advantages from both PET and Prompt Gamma Imaging (PGI). The technology would also be of importance for other applications, such as total body diagnostic PET or a combined PET/SPECT scanner, or other nuclear imaging fields. The combination tackles the main limitations of both in-beam PET and PGI, by making it possible to fuse the two imaging techniques in a single device.

Further objects and advantageous features of the invention will be apparent from the claims and the following detailed description of embodiments of the invention in relation to the annexed drawings.

BRIEF DESCRIPTION OF THE FIGURES

FIG. 6a is perspective schematic view of a detection module of a detection module assembly of a gamma ray detection system according to an embodiment of the invention;

FIG. 6b is a view similar to FIG. 6a with some photon sensor support boards and photon sensors removed to see an inner portion of the detection module;

FIG. 6c is a detailed schematic cross-sectional view of a portion of a scintillator plate of a detection module according to an embodiment of the invention;

FIG. 8a is a simplified schematic view of a portion of a detection module assembly of a gamma ray detection system according to an embodiment of the invention, illustrating detection of a positron annihilation (corresponding to a PET scanner function);

FIG. 8b is a view similar to FIG. 8a illustrating detection of a prompt gamma ray (corresponding to a Compton camera function);

FIG. 9a to FIG. 9c are schematic perspective views illustrating stacked scintillator plates of different shapes, for a detection module according to different embodiments of the invention;

FIG. 10 is a simplified schematic view of a detection module of a gamma ray detection system according to an embodiment of the invention, showing a scintillator plate arrangement;

FIG. 11a is a simplified schematic side view of a detection module, illustrating an arrangement of photon sensors according to an embodiment of the invention;

FIGS. 11b to 11e are further views similar to FIG. 11a of further different embodiments of photon sensor arrangements according to the invention;

FIGS. 12a to 12c are simplified schematic views of photon sensor arrangements of detection modules according to various embodiments of the invention for functioning inter alia as a Compton camera;

FIG. 13a is a simplified schematic view of a photon sensor arrangement of yet another embodiment of the invention for functioning inter alia as a Compton camera;

FIG. 13b is a view similar to FIG. 13a of yet another embodiment functioning as a Compton camera;

FIGS. 14a and 14b are simplified schematic views of a pair of detection modules of a detection module assembly according to embodiments of the invention whereby adjacent modules function as an inter-module Compton camera according to an embodiment of the invention;

FIGS. 16a and 16b are simplified schematic perspective views of detection module assemblies according to different embodiments of the invention, FIG. 16a illustrating a dual head assembly and FIG. 16b illustrating a triple head assembly, capable of functioning as a Compton camera for prompt gamma ray detection and as a PET scanner for detection of positron annihilation;

FIGS. 20a and 20b are simplified schematic views of a scintillator plate of a detection module comprising an electro optical shutter (EOS), FIG. 20a showing the EOS open and FIG. 20b showing the EOS closed;

FIG. 20c is a simplified schematic perspective view of an example of a stack of scintillator plates where the top and bottom layers have an open EOS and the three middle layers a closed EOS;

FIG. 21a is a schematic simplified perspective view of a scintillator plate with individual photon sensors;

FIG. 21b are plots illustrating the mean number of photons detected by a single photon sensor along the right edge subsequent to a scintillation event;

FIG. 27 is a schematic illustration of a detection module assembly of a gamma ray detection system according to an embodiment of the invention used for triangulating the source position of a tri-gamma event;

FIG. 28 is a schematic illustration of sensor plates in an azimuthal-axial arrangement according to an embodiment of the invention;

FIG. 29 is a schematic illustration of a multiplexed readout of a 2×2 azimuthal-axial arrangement of sensor plates according to an embodiment of the invention;

FIG. 30 is a schematic illustration of how rearrangement of axially-azimuthally arranged sensor plates enables a larger field of view;

FIG. 34 show plots of detection probability for different energies, total radial scintillator thickness and scatter/absorber relations for a 2 radial layer-configuration according to embodiments of the invention;

FIG. 35 shows a plot of the coordinate component of the angular precision for Compton reconstruction for various combinations of radial gap and scintillator plate thicknesses according to embodiments of the invention;

Figure 1:
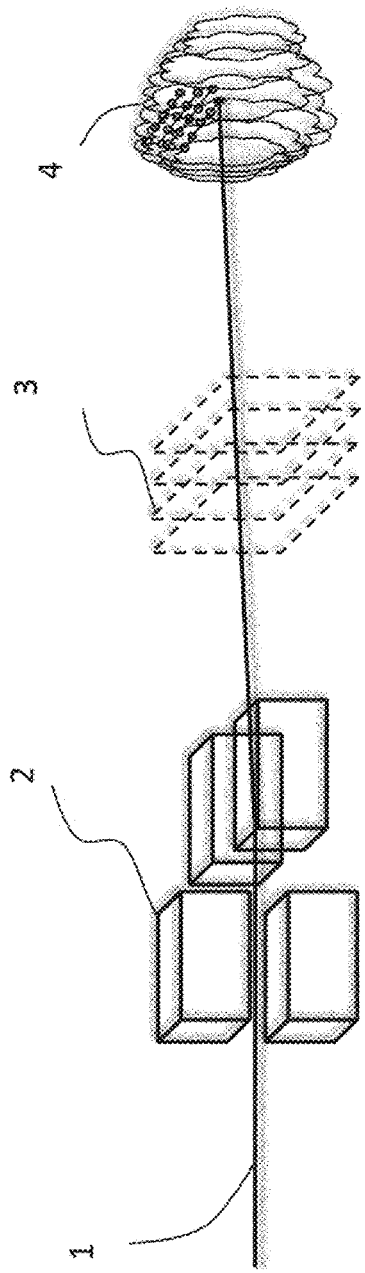
FIG. 1 is a schematic illustration of a typical ion beam setting.
Figure 2:
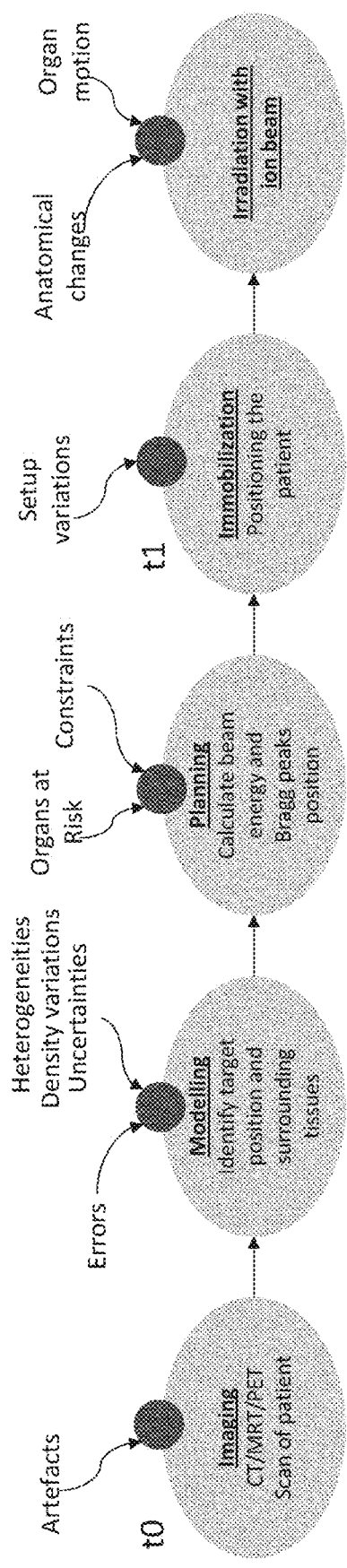
FIG. 2 is a flowchart of a conventional ion beam irradiation preparation plan, showing errors and factors that can cause range uncertainty in irradiation treatment according to conventional therapy.
Figure 3:
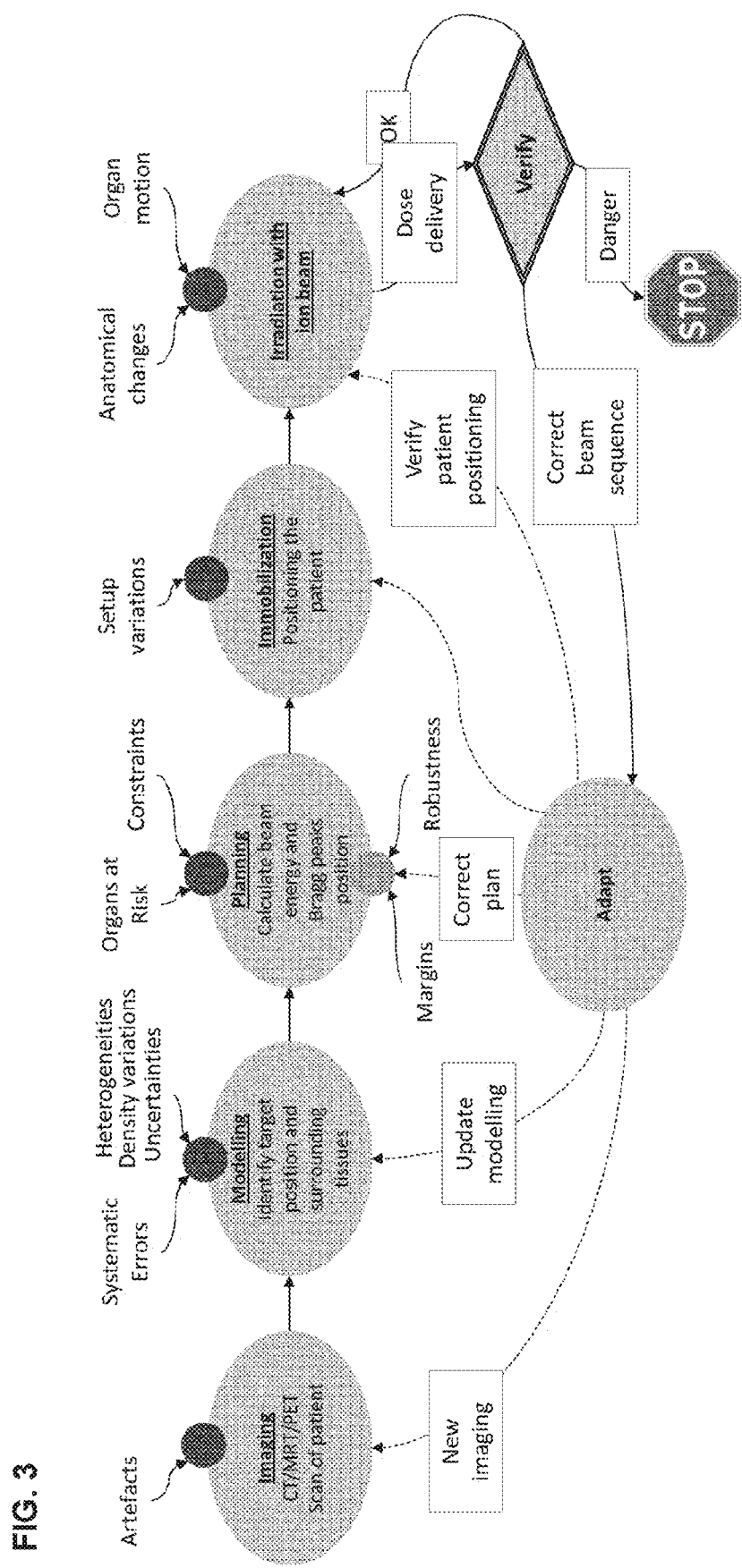
FIG. 3 illustrates a flowchart of an ion beam irradiation preparation plan, showing errors and factors that can cause range uncertainty in irradiation treatment, and corrective measures implemented in accordance with an embodiment of the present invention to reduce range uncertainty and improve dose accuracy.
Figure 4:
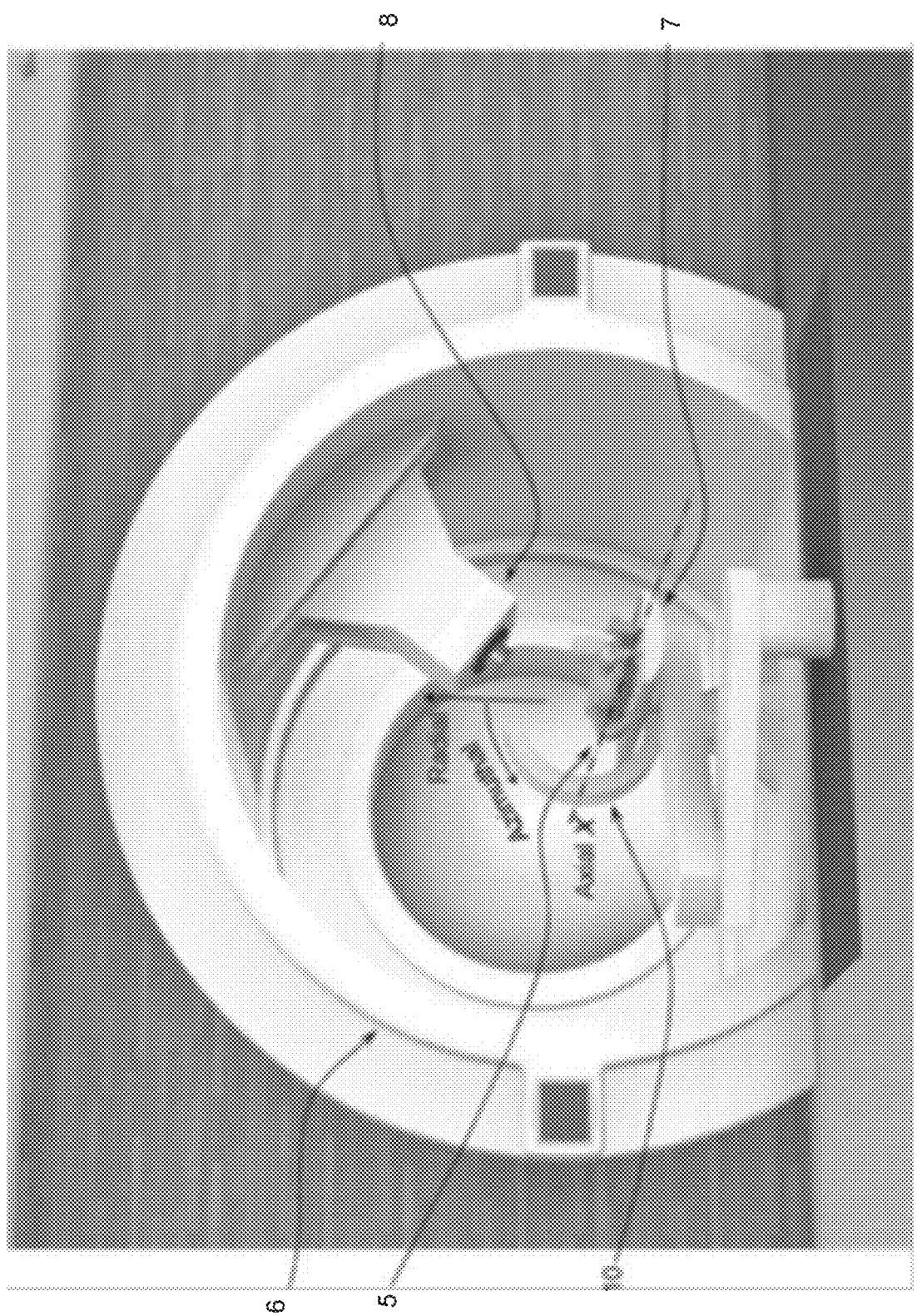
FIG. 4 is a perspective illustration of an ion beam therapy system with a gamma ray detection system, according to an embodiment of the invention.

Referring to the figures, starting with FIG. 4, an ion beam therapy system 6 in particular for ion beam radiotherapy, or for proton beam irradiation of a zone of tissue, according to an embodiment of the invention is illustrated. In this embodiment, a patient 5 is positioned on a patient support 7 that is mobile relative to an ion beam emitter 8 at least about an axis of rotation and a translation. The patient support 7 may in particular be movable at least in translation along at least one axis, in particular a horizontal axis X relative to a fixed reference (for instance ground), and the ion beam emitter may be rotatable around said horizontal axis X relative to a fixed reference (for instance ground). The patient support and/or the ion beam emitter may however be movable in translation and/or rotation along and around a plurality of axes, up to a fully three dimensional movement allowing the ion beam emitter to be positioned at any position and angle relative to the patient.

The ion beam therapy system further comprises a gamma ray detection system 10. The gamma ray detection system 10 may, in certain embodiments, also be relatively movable with respect to the patient support along or around one or more axes. In an embodiment, the gamma ray detection system is movable one along at least a direction of translation, in particular along the axial direction, and in a variant also in rotation in the azimuthal direction in coordination with the ion beam emitter 8.

In variants (not illustrated), it is however possible to have a gamma ray detection system that is static with respect to a fixed reference, or that moves only in translation with respect to a fixed reference such as ground.

In a preferred embodiment, the gamma ray detection system 10 comprises a detection module assembly 13 that is generally ring or polygon shaped. In an embodiment, the detection module assembly may comprise an opening 42 to allow the ion beam emitter 8 to transmit ions (e.g. protons) through the opening such that the direction of emission of the ion beam emitter 8 is substantially in the same plane as the detection module assembly. This provides for a simultaneous and efficient detection of gamma rays emitted from the target zone receiving the ion beam. The detection module assembly 13 may for instance have a general "C" shape to provide an opening between opposed ends of the C shape to allow the ion beam emitter 8 to transmit ions through the opening. However, in variants, a substantially closed ring/polygon shape may be provided, for instance a generally cylindrical detection module assembly, with an orifice through a portion thereof to allow the ion beam to be transmitted therethrough (variant not illustrated).

The length of the detection module assembly 13 in the direction of the axis of rotation X of the ion beam emitter 8 (herein also referred to as the axial direction), may range from around 5 cm to around 200 cm depending on the variant. For detection configurations with shorter axial lengths, a translation of the detection module assembly 3, possibly in conjunction with the ion beam emitter, may be effected during ion beam therapy. The detection module assembly may also be translated for scanning of the target zone, after ion beam emission, or during diagnosis, according to an embodiment. With detection module assemblies having a length sufficient to extend over the entire target zone, it is possible to have a detection module assembly that is static with respect to the patient, whereby a displacement of the ion beam or ion beam emitter may not be followed by the detection system.

It may further be noted that the movement of the detection module assembly may be parallel or corresponding to the movement of the ion beam emitter or may follow a different movement configured to optimize the detection of prompt gamma rays and positron annihilation gamma rays emitted from the target as a function of the position of the target, the target environment, and the position and angle of inclination of the ion beam emitter 8. The optimal movements of the ion beam emitter and of the detection system may inter alia be obtained from calibration of the system on sample tissue.

An important advantage of the gamma ray detection system 10 used in the ion beam therapy system 6 according to embodiments of the invention, is that detection can be performed in real time during proton beam emission, capturing both prompt gamma rays as well as positron annihilation gamma rays. In addition the positron annihilation gamma rays that are emitted during a certain time after proton beam emission, or between successive proton beam emission pulses during treatment, may be detected. This allows the proton beam absorption relative to the target zone to be continuously monitored, and with feed back from the detection system, to be adjusted in order to have precise targeting of the target zone taking into account any movements of the target zone during treatment or after treatment and avoid other problems such as wash out effects and the like that have been discussed previously in relation to conventional systems.

The prompt gamma rays emitted from the volume of interest may be detected with the detector functioning as a Compton camera whereas the positron annihilation gamma rays of generally lower energy (511 keV) may be detected with the detection modules using a PET scanner functioning principle, both of these detection methods being integrated in the detection modules of the detection assembly according to embodiments of the invention as will be further described hereinafter. It may be noted that the PET detection may be operated during the ion beam emission, between ion beam emissions and after ion beam emission, or alternatively may be switched on only between and after ion beam emission pulses. During ion beam emission, the rate of prompt gamma ray emission is very high which may render the measurement of coincident gamma rays from positron-emission annihilation less accurate and reliable, whereas for a certain duration after ion beam emission, prompt gamma ray emissions are low and positron annihilation gamma ray emissions continue for a certain time (as per se well-known) such that measurements can be performed during and after ion beam emissions.

Figure 5B:
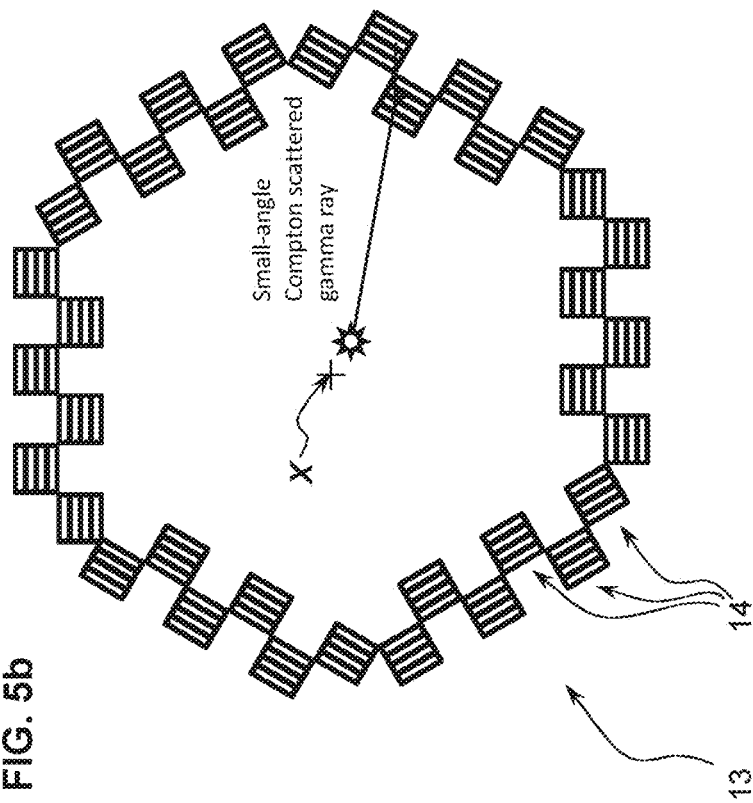
FIGS. 5a to 5e are schematic illustrations of five variants of a detection module assembly of a gamma ray detection system according to embodiments of the invention.
Figure 5A:
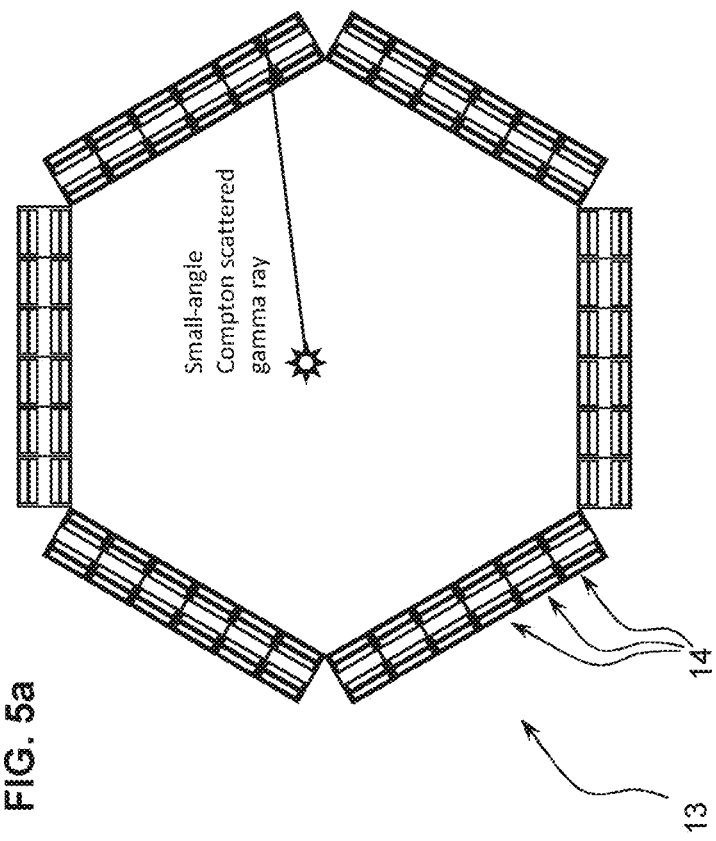
Figure 5D:
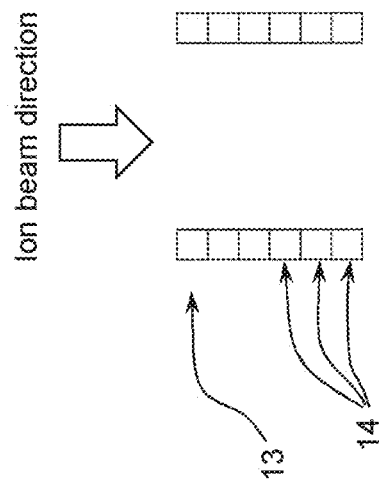
Figure 5C:
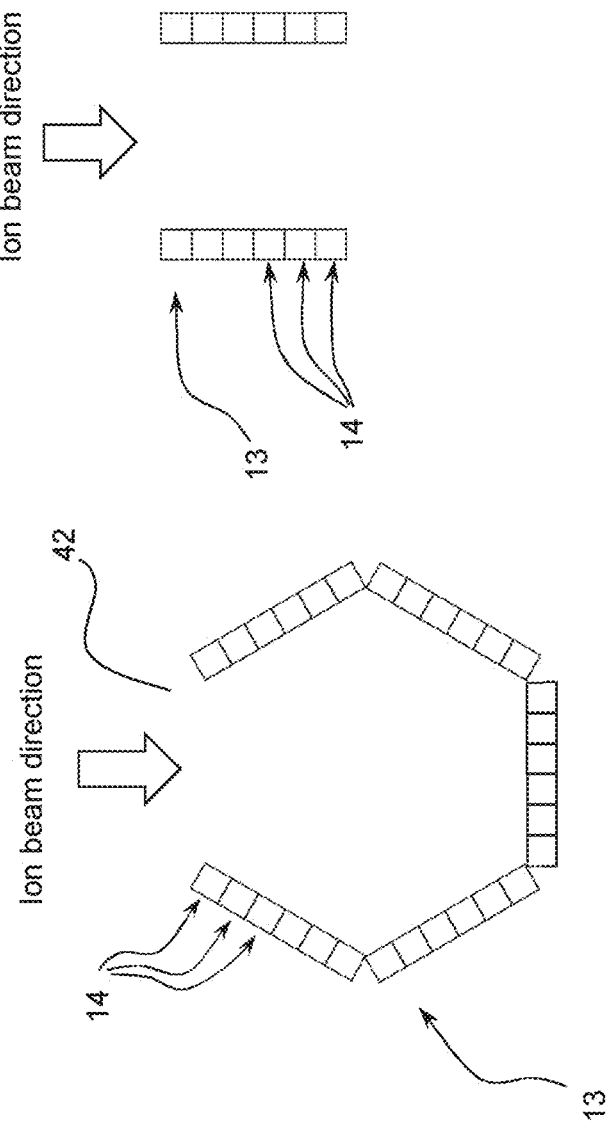
Figure 5E:
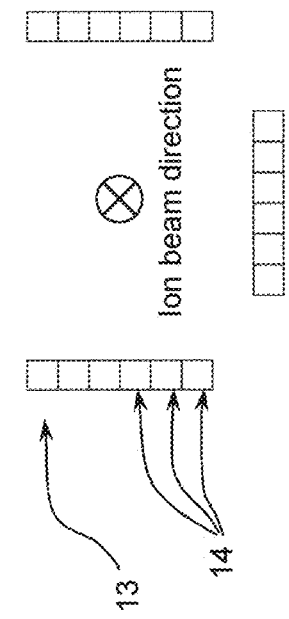

Referring to FIG. 5a and FIG. 5b, two different embodiments of a detection module assembly 13 of a gamma ray detection system 10 according to embodiments of the invention are schematically illustrated. Although the detection module assembly 13 in these illustrations is shown as substantially fully closed ring/polygon shape, it is understood that a section thereof may be removed in order to provide a substantially "C" shape with an opening for an ion beam emitter to transmit ion beams therethrough to the target zone. It is also understood that the detection module assembly 13 may comprise spatially separated detection modules, for example a "dual-head" configuration (FIG. 5e) or "quad-head" configuration (FIG. 5f).

The detection module assembly 13 comprises a plurality of detection modules 14. The detection modules 14 may, in an embodiment as illustrated in FIG. 5a, be arranged in an aligned manner to form segments, or in another embodiment as illustrated in FIG. 5b, be radially staggered, the radial direction beam considered from the rotation axis X. Various other configurations are however possible, whereby the number of modules aligned to form a segment or positioned in a substantially circular arrangement or in a polygonal arrangement (as illustrated) may be varied.

The detection modules 14 are configured to function as both a Compton camera 11 and a PET scanner 12 as will be described in more detail further herein. It is however possible to use the detection modules of the present invention only functioning as a Compton camera or only functioning as a PET scanner, depending on the application.

Each detection module 14 comprises a plurality of stacked scintillator plates 16 and a plurality of photon sensors 18. The scintillator plates have a major surface 40a oriented to generally face the target zone or axis X, and lateral minor surfaces 40b defining the edges or contour of the scintillator plates. For simplicity, the lateral minor surfaces 40b shall also be named herein "edges". In embodiments (not shown) it is also possible to add one or more detection modules at an axial end of the target zone or imaging volume of interest, or at an intermediate position between the axial end and radial position. In one advantageous embodiment, the stacking direction of the scintillator plates in the detection module 14 is orthogonal to the major surface. The photon sensors 18 are positioned on the edges of the scintillator plates 16.

The detection module may comprise, according to embodiments, a stack of scintillator plates without a radial gap, or according to other embodiments, a stack of scintillator plates including at least one radial gap 17.

The radial gap 17 is in particular useful for the functioning of the Compton camera 11, whereby some scintillator plates act as scatterer Compton camera, and another scintillator plate act as absorber. Compton kinematic rules, or timing, may be applied to determine the scattering and absorber layers.

The interface between the scintillator plates may comprise an interlayer reflector 28 that is light reflective to conduct light from a scintillation event to the scintillator plate edges, while allowing gamma rays to pass therethrough.

Instead of an interlayer reflector, or in addition to an interlayer reflector, the scintillator plates may be separated by a low refractive index gap or gaps 31, for instance of air or of a low refractive index solid such as a polymer material. The low refractive index gap 31 has the effect that the surface of the scintillator plate acts as an internal reflector to improve transmission of light from a scintillation event to the scintillator plate edges while allowing gamma rays through the layers. In addition or as an alternative to the interlayer reflector, a light barrier or absorber layer 29 may be inserted between the scintillator plates in combination with low refractive index gaps to prevent interlayer light pollution.

The reflective or absorbent interface layer may constitute a coating on one side of the scintillator plate or on both sides of the scintillator plates that are stacked together.

The major surface 40a of the scintillator plates is the surface upon which the gamma rays are generally incident, and the edge 40b, which may be for instance substantially orthogonal to the major surface and extends between opposed sides of the scintillator plate, forms the edge of the scintillator plate along which the photon sensors 18 are arranged. The surface area S of the major surface of the scintillator plate and the thickness T may, in preferred embodiments of the invention, lie in the ranges:

100 mm$^2$<=S<=40000 mm$^2$, and
0.5 mm<=T<=30 mm;
more preferably
400 mm$^2$<=S<=40000 mm$^2$, and
1 mm<=T<=10 mm.

The preferred ranges seek to optimize the relationship between the accuracy of the depth of interaction (DOI) measurement (Z direction) and/or reduction in the number of readout channels on the one hand, and the accuracy of detection in the major surface of the scintillation plate (X-Y plane) of the scintillation position. Optimal ranges may vary depending on the application.

Along edges 40b of the scintillator plates, an edge light spreader material layer 26 may be provided. The function of the edge light spreader material 26 is to spread the gamma rays such that the light from gamma rays incident on the scintillator very close to one edge 40b is distributed over several adjacent photon sensors.

The edge 40b of the scintillator plate may further be provided with a detector-scintillator optical interface 22 comprising an interface material that optimizes optical transmission through the edge to the photon sensors and/or provides a consistent and predictable transmission of photons through the layer to avoid inconsistencies that may occur due to a non-constant interface (e.g. due to air, variable gaps and the like). The optical interface also serves to spread out the light from a scintillating event occurring close to the scintillator edge over multiple photon sensors in order to improve spatial resolution.

Along one or more of the scintillator plates, an electro optical shutter (EOS) 24 may further be provided that is electronically operated to be switched on (optically transparent, 24a) or off (absorbing or reflecting, 24b), in order to allow photons to pass through the edge to the photon sensor or to be blocked from passage to the photon sensor, depending on the state of operation of the detection module 14.

The height H of the radial gap 17 in relation to the thickness T of one scintillator plate may typically be in the range of 200>H/T>2,
preferably in a range of 50>H/T>10.

In a variant, different sensor plates may have different thicknesses of the scintillator plates. For example, radially inner scintillator plates, primarily acting as Compton scatterers, may be thinner to reduce the probability of absorption or re-scattering of a gamma ray Compton scattered in a radially inner layer. Radially outer scintillator plates may be thicker to increase the probability of total absorption. Scintillator plate thicknesses may vary as a function of radial position, or radially sequential position.

The height H of a radial gap 17 in relation to the thicknesses T1 and T2 of two scintillator plates radially surrounding the gap may typically be in the range of 100>H/(T1+T2)>1, preferably in a range of 25>H/(T1+T2) >5.

It may be noted that the radial direction referred to herein corresponds to the direction Z indicated in the figures illustrating a detection module.

The photon sensors 18 arranged along the edges 40b of the scintillator plates 16 may be provided on a photon sensor support board 20 that may for instance be in the form of a circuit board with circuit traces for interconnecting the photon sensors to a signal processing and control system 30 of the detection module 14. The support board 20 may also be a flexible or rigid flexible circuit. The flexible circuit may cover one or more edges of a module, and be folded around and optically coupled to the edges of a radial stack of scintillator plates. In order to minimize dead space between detection modules, it is advantageous to make the photon sensor support board thin.

The support board may include protruding guiding elements to facilitate alignment of the scintillator edges with respect to the photon sensors.

Figure 6D:
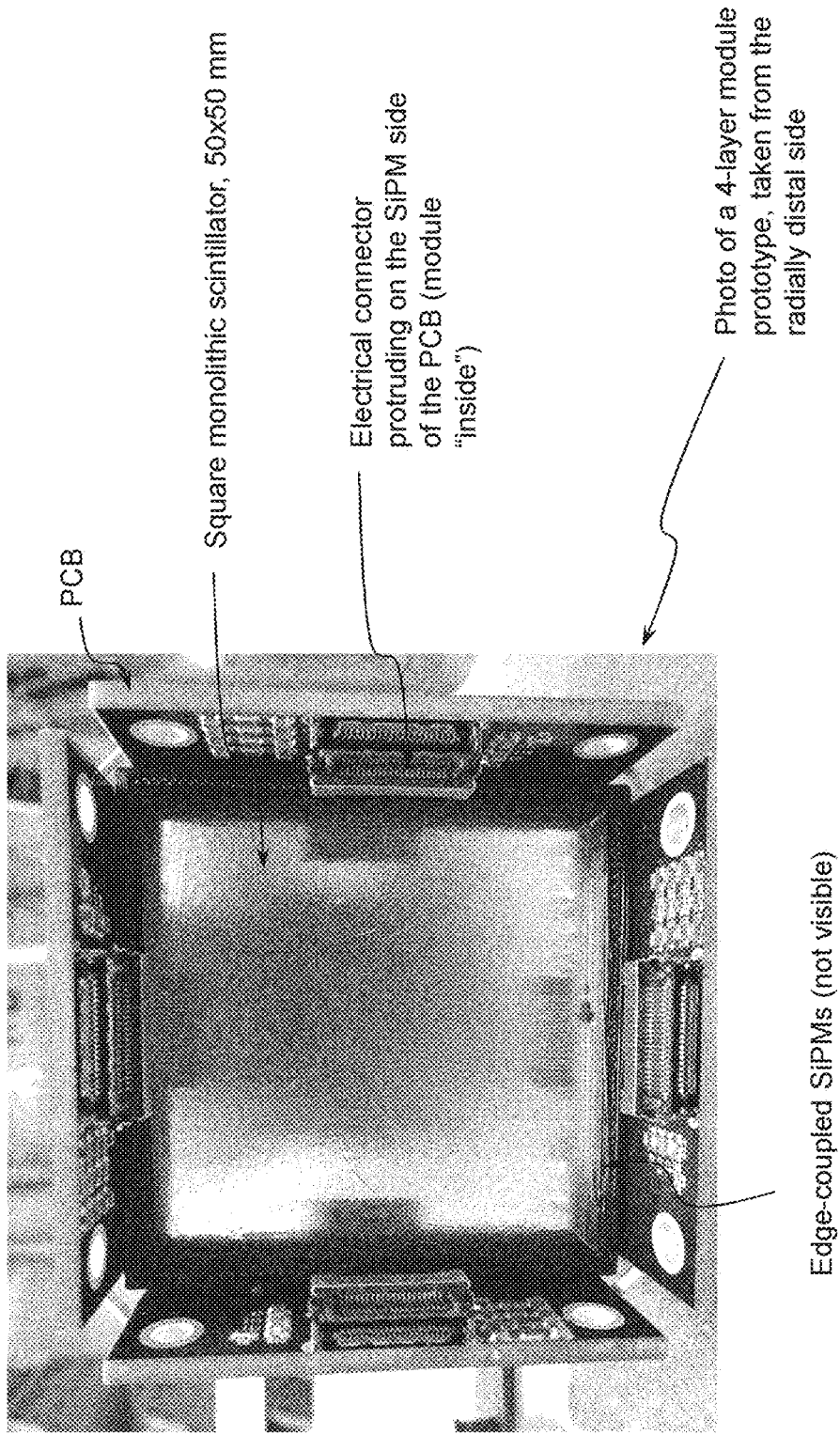
FIG. 6d is a photograph of a prototype detection module according to an embodiment of the invention with four radially stacked sensor plates, taken from the radially distal side.
Figure 7:
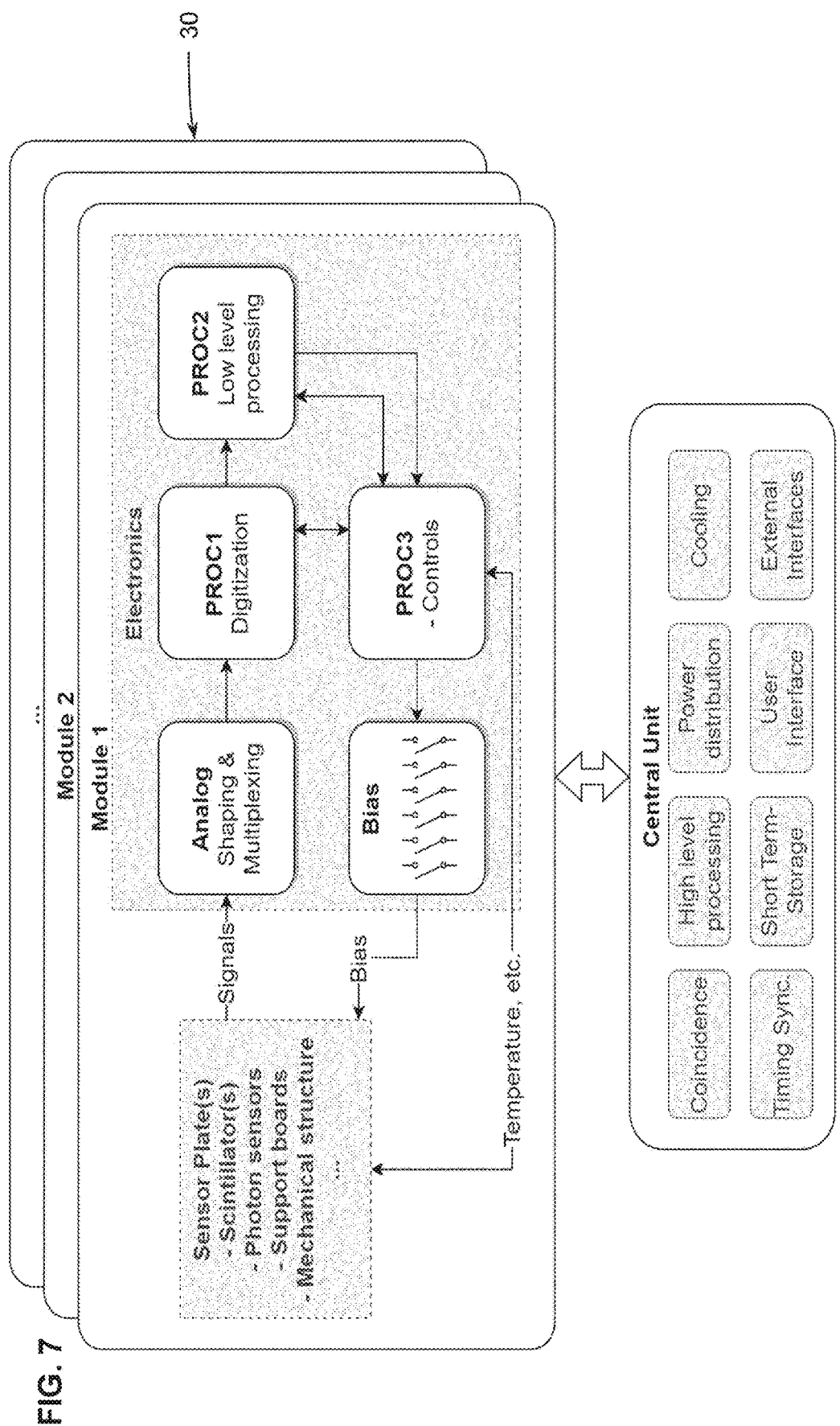
FIG. 7 is a schematic illustration of detection modules, comprising sensor plates and signal processing and control modules, of a gamma ray detection system according to an embodiment of the invention.

The signal processing control system 30 of the detection module 14 may comprise for instance a circuit board 32 and electronic components 34 mounted thereon, including for instance analog components for signal filtering, signal shaping, multiplexing and combinations of individual photon sensor signals, and photon sensor bias voltage components, a microprocessor and a memory for processing and control of the detection module. The circuit board 32 may be mounted at an outmost radial end of the module and comprise connectors 36a, 36b for connection of the circuit board 32 to the photon sensor support boards 20 and further to an electronic control system of the gamma ray detection system 10 for image reconstruction, as best illustrated in FIG. 7 in conjunction with FIG. 6a and FIG. 6b. The support boards 20 may be configured as silicon photomultiplier array boards with edge connectors 36b that advantageously minimize the gap between adjacent detection modules 14 of the detection module assembly 13.

In a variant, some analog components, for example signal shaping components, filtering components or signal multiplexing components, are mounted directly on the photon sensor support board, in close proximity to the photon sensors.

Signal processing components comprise components for analog signal digitization, such as triggering, timestamping, and energy measurements (for example charge integral or time-over-threshold). Additional processing components may be low level event processing for event validation or event rejection, using pre-determined or configurable rules based on, for example, Compton kinematics, photon sensor thresholds, energy thresholds, number of sensor plates or photon sensors coincidentally triggered, or other applicable rules determined from prior detector calibrations.

Analog and digital signal processing components may be distributed to be connected to more than one radial stack of sensor plates, i.e. one or more radial stacks of sensor plates may "share" analog and digital signal processing components.

The photon sensors 18 may comprise individual layer photon sensors 18a and/or strip multi-layer photon sensors 18b. In certain embodiments, the photon sensors 18 may comprise both strip multi-layer photon sensors 18b that extend radially (in the Z direction) across the edges of a plurality of stacked scintillator plates 16, and individual layer photon sensors 18a that are positioned on individual scintillator plates. A detection module 14 may comprise a plurality of strip multi-layer photon sensors 18b on each side of the module and in addition a column of individual layer photon sensors 18a on each side of the module or on only some of the sides, or on only one side depending on the variant as illustrated for instance in FIG. 17a to FIG. 17e. The individual layer photon sensors 18a enable the determination of the layer or layers in which the incident gamma ray is absorbed, whereas the multilayer strip photon sensors 18b (possibly in combination with the illuminated individual layer photon sensor) enable the position of incidence of the absorbed gamma ray to be determined within the plane orthogonal to the radial direction (i.e. a plane parallel to the major surface 40a of the scintillator plate 16).

An important advantage of the use of strip multi-layer photon sensors 18b is to reduce the number of channels that need to be processed by the signal processing and control electronics for a given number of stacked scintillator plates, without reducing measurement accuracy. Thus, the data processing requirements are significantly reduced as well as the associated costs of the equipment, or alternatively greater accuracy in the depth of interaction measurement is obtained by having a larger number of stacked scintillator plates for a given number of readout channels.

Figure 18:
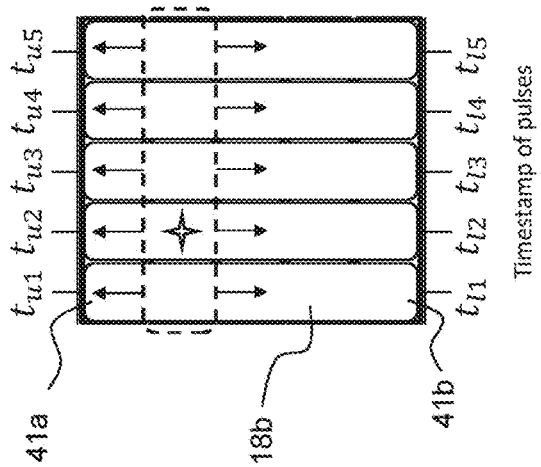
FIG. 18 is a simplified schematic view of a photon sensor arrangement of a detection module of a gamma ray detection system according to yet another embodiment of the invention with photon strip detectors.

In a variant, as best illustrated in FIG. 18, instead of providing individual layer photon sensors 18a to determine the depth of interaction, there may be provided only strip multi-layer photon sensors 18b extending across the stack of scintillator plates, however these strip multi-layer photon sensors are configured to measure the time difference between ends of the strip multilayer photon sensors, which is related to the position of the illumination along the strip, from which the layer where the scintillating event occurred can be deduced.

Figures 19A, 19B, 19C:
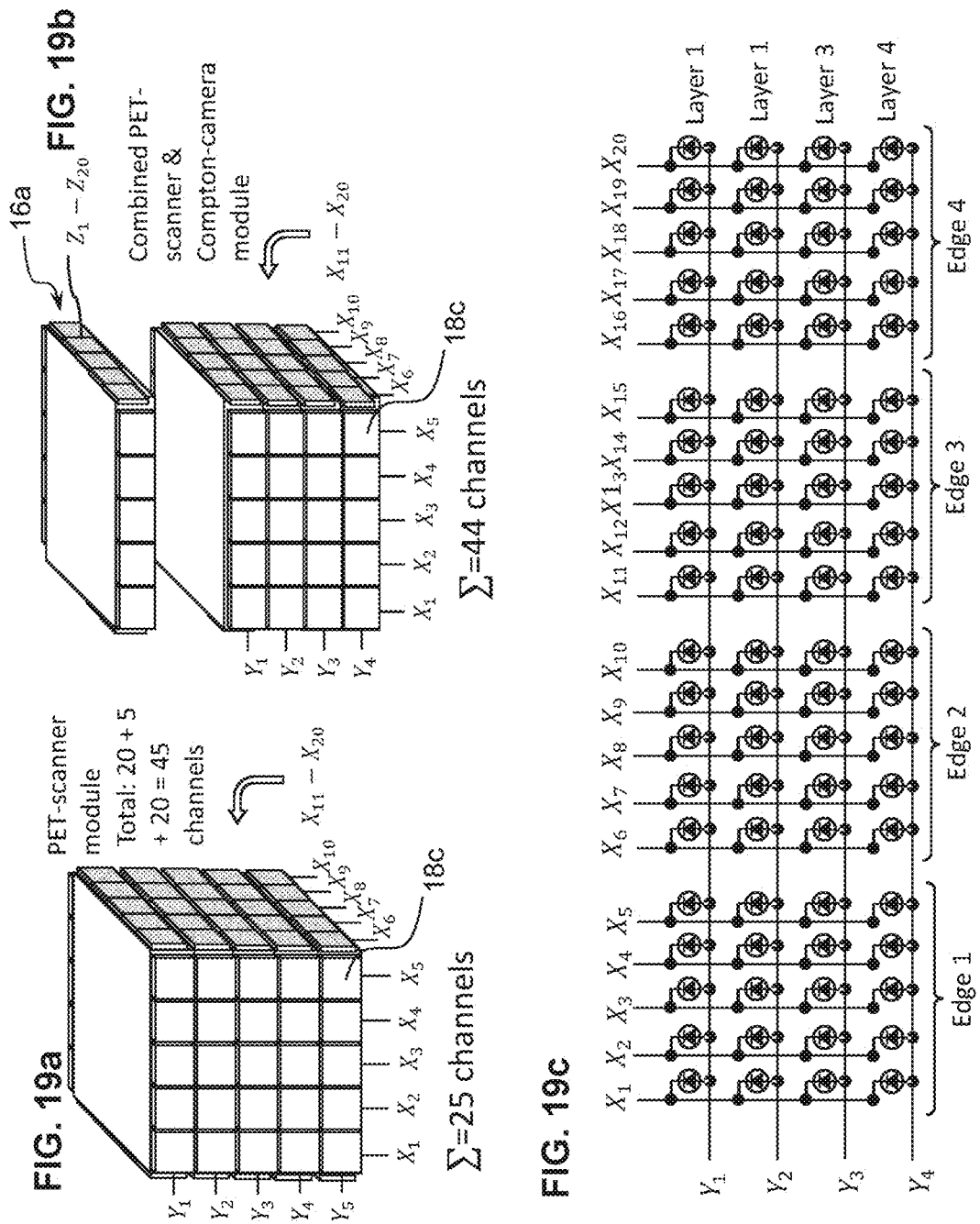
FIGS. 19a and 19b are perspective views of two different detection modules of a gamma ray detection system according to yet further embodiments of the invention, illustrating photon sensor configurations with cross-wire connection arrangements for a cross-wire readout.
FIG. 19c is a simplified circuit diagram of a cross-wire connection readout of the embodiments of FIG. 19a and FIG. 19b.

In yet another embodiment in order to reduce the number of readout channels, individual layer photon sensors 18a arranged in columns may be interconnected in a cross-wire connection configuration, or in a resistive network, or, in general, a multiplexed manner, as best illustrated in FIG. 19a to FIG. 19c, thus allowing the number of channels to be reduced. It may be noted that the diodes in the example of FIG. 19c represent SiPMs (Silicon photomultipliers). The multiplexed readout enables measurement of the position of scintillation in a scintillator plate to be determined by the intersection between rows and columns of the individual layer photon sensors while having a reduced number of channels to be electronically processed. The electro-optical shutter as schematically illustrated in FIG. 20a to FIG. 20c allows a certain number of scintillator plates to be optically blocked during very high rates of prompt gamma emissions in order to prevent that the photon sensor signals from multiple sensor plates triggered coincidentally are superimposed in the multiplexed readout, which would destroy the information from individual triggered sensor plates.

With digital silicon photomultipliers as photon detectors, it would be possible to enable/disable individual cells of the strip photon detectors in order to mask (ignore) the light originating from selected scintillator layers. This is an alternative to achieve the same functionality as optical shutters.

Figure 15B:
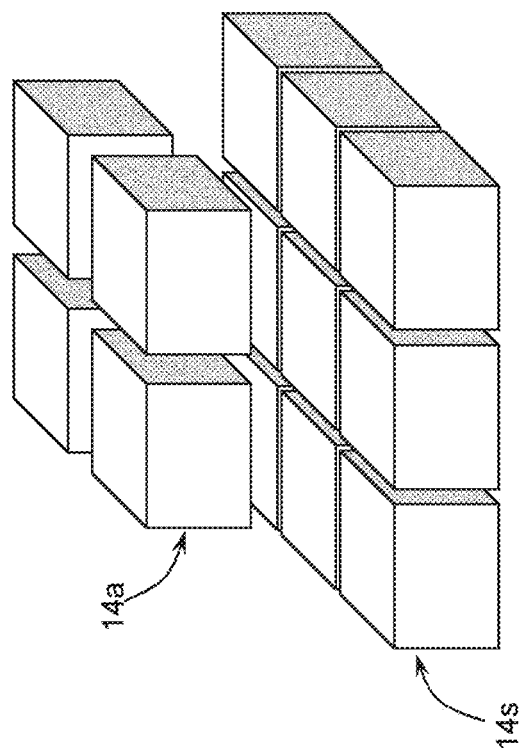
FIGS. 15a and 15b are simplified schematic perspective views of a detection module assembly according to embodiments of the invention that may function as a PET scanner and a Compton camera.
Figure 15A:
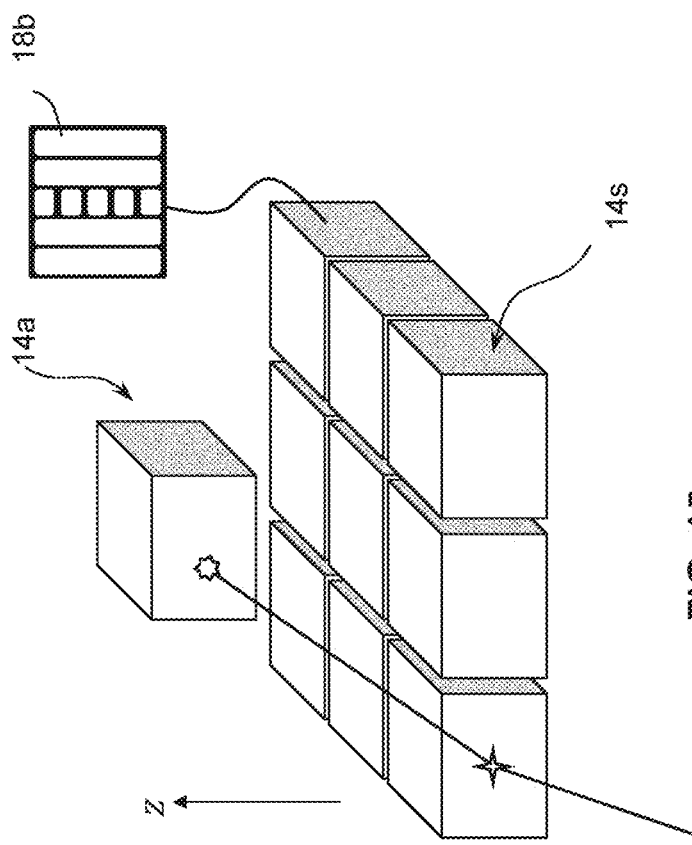

It may be noted that in a Compton camera arrangement, the detection modules 14 may comprise a plurality of scatter sensor plates 14s of a greater number and surface area than the absorber modules 14s as illustrated in FIG. 15a and FIG. 15b. The positron emission tomography scanner function is in such configuration performed by the larger plurality of modules 14s radially closer to the target zone, whereas the absorber modules 14a positioned radially further from the target zone act as absorber modules for a Compton camera functioning. Such arrangement also allows the functioning of both the Compton camera and PET scanner simultaneously while further reducing the number of readout channels for signal processing.

The PET-scanner functionality of embodiments of the invention may thus be achieved using a stack of monolithic scintillator crystals. The scintillating light is propagated from the point of interaction toward the sides, where it is detected by a plurality of photon-detectors. The photon sensor can for instance be SiPM (analog or digital) or other types of per se known detectors. To improve spatial resolution for events that are located close to the sides of the scintillators, an optical (non-scintillating) "spreader" material 26 may be inserted between the scintillator and the photon sensors as previously mentioned. This causes the light emitted by the gamma-interaction to spread over multiple pixels, even when the interaction occurs close to the scintillator side. Examples of spreader material may include glass, silicon rubber or the like, and thicknesses can vary, whereby different spreader shapes may be implemented to optimize light yield on the photon sensors. Instead of, or in addition to, a spreader material, a thin interface optical layer 22, for instance comprising a grease, glue, or meltmount may be provided between the scintillator plate edge 40b and the photon sensor as previously mentioned.

The propagation of light from the point of interaction toward the photon sensor may occur through total internal reflection. This can be achieved by inserting a material of lower index of refraction between the scintillator plates, e.g. air. Using air has the advantage of not posing any particular manufacturing constraint, and it does not degrade with time, use or due to radiation. Another feature would be to stack the scintillator plates together with a highly reflective material or film in between layers (e.g. ESR=Enhanced Specular Reflector). Care should be taken that the reflectivity remains sufficiently stable during the operational conditions of the device, and/or in between foreseen device calibrations.

Since the signal from individual layers can be resolved in embodiments of the invention, the PET-scanner functionality has inherent depth-of-interaction capability. The depth-resolution is primarily given by the thickness of the scintillator plate. The thinner the plates, the better the DOI (Depth of interaction)-resolution. However, as the number of plates 16 increases, the number of photon sensors 18 that are required also increases. To alleviate this problem, embodiments of the invention include the use of elongated photon sensors, namely the previously mentioned multilayer strip photon sensors, stretching over multiple scintillator edges. One single channel can thus measure the light from multiple scintillator plates. In order to resolve in which scintillator plate the interaction occurred, single-plate pixels are included in at least one photon sensor column per side, namely the previously mentioned individual layer photon sensors.

The number of layers the strip detectors cover may be tailored to the foreseen event-rate range: for low count-rate applications, the likelihood of multiple gamma-interactions occurring in several layers "simultaneously" (e.g. during the coincidence window, or during the response time of the photon sensors) would be negligible. For SiPMs, the practical dead-time between events is typically in the order of several 100s of nanoseconds.

In Compton camera imaging, one typically employs a first "scattering" layer, where X-rays/gamma-rays interact via Compton scattering and a fraction of their initial energy is deposited, $E_1$. An X-ray/gamma-ray is emitted at an angle $\theta$ that is slightly different from the initial direction, the angular change being related to the energy deposited. This photon is absorbed in a second scintillator plate, the "absorber".

By calculating the energy deposition in the two scintillator plates, $E_1+E_2$, and the interaction coordinates in the two layers, one can infer information about the initial position of the initial ray.

$$\cos\Theta = 1 - m_0 c^2 \left( \frac{1}{E_2} - \frac{1}{E_1 + E_2} \right)$$

where $m_0$ is the mass of an electron, c is the speed of light. For energy discrimination, one typically requires that the measured energy deposition $E_1+E_2$ matches a prompt gamma emission peak of one (or several) isotope states of interest in order to reduce the probability that the gamma ray detected in the first layer has been previously Compton scattered, for example in the patient.

It is necessary to measure the coordinates of interaction in the two layers, from which the angle can be determined. Unlike PET reconstruction, where a LOR can be drawn between the interaction coordinates in the coincident scintillation events, Compton imaging yields a "cone", emanating from the interaction point of the scattering layer, with a direction and opening angle given by the energy and coordinate information from the two separate layers.

Figure 41:
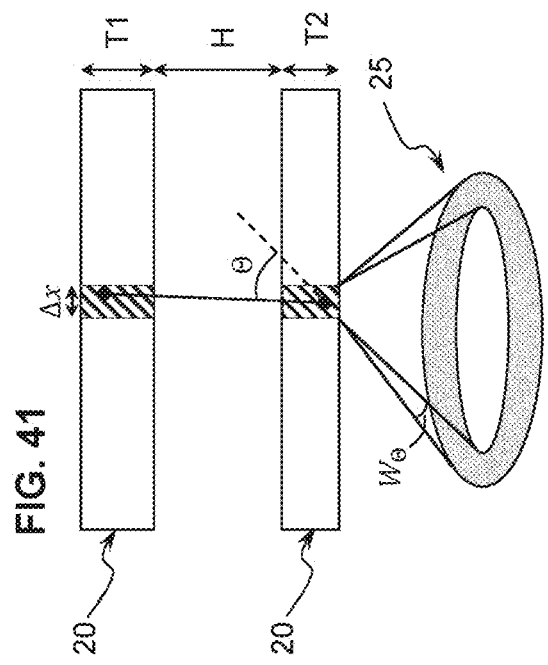
FIG. 41 illustrates the impact of energy and spatial uncertainty on Compton-scattering angle reconstruction.

When the detector acts as a Compton camera, its angular precision is mainly determined by two components: (1) the energy precision with which $E_1$ and $E_2$ may be determined, and (2) the spatial coordinate accuracy that defines the line between the absorption event and scatter event, the latter from which the Compton cone with an angle $\theta$ is generated for image reconstruction, as illustrated in FIG. 41. A detailed study comparing the magnitude of these two components was made, summarized in FIG. 35 (coordinate component only) and FIG. 37 (coordinate and energy component), under the following assumptions:

The energy precision is approximately proportional to the square root of the deposited energy, and assumed to be approximately 10% at 511 keV for e.g. LYSO.

The spatial coordinate precision $\Delta x$ is $\pm 0.7$ mm in both the azimuthal and axial direction (X-Y)

As these two components are largely independent, they may be added in quadrature. The energy precision is a fundamental limit—intrinsic to the scintillating crystal material, and limited by the photon sensor energy resolution—that is challenging to overcome. One may therefore take proper care that the contribution from the spatial coordinate precision is at least well below the energy component. At H/T>=10, this is largely achieved e.g. for most of the energies of interest for Prompt Gamma imaging in proton therapy.

Figure 37:
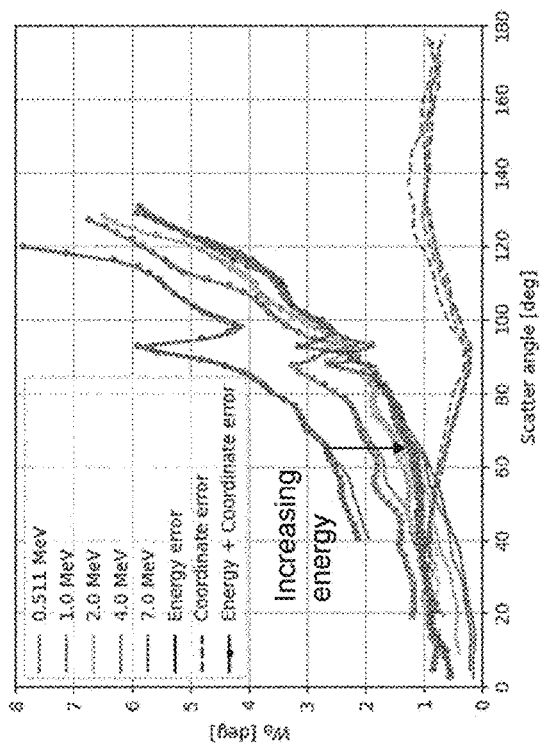
FIG. 37 shows a plot illustrating the angular precision of the Compton scattering angle reconstruction, and the contribution from limitations in energy resolution, and limitations in spatial resolution according to embodiments of the invention.

FIG. 37 illustrates the angular precision as a function of scattering angle for energies between 0.511 and 7.0 MeV at H/T=10. For a scattering angle above approximately 40 degrees, the overall angular precision (solid lines with markers) is dominated by the contribution from energy resolution (solid lines), whereas the contribution from coordinate precision is less important (dashed lines).

The angular precision deteriorates significantly for large-angle scattering, and in particular back-scattered events ($\Theta$>90 degrees). It would therefore be beneficial to implement rejection of events where the reconstructed scatter angle exceeds some configurable value, in order to improve the image quality. Different upper thresholds may be used for different energies. The threshold may be implemented as energy discrimination thresholds in the absorber or scatter scintillator plates, or as an actual angular threshold to be applied after scatter angle reconstruction.

In order to accurately determine the transverse coordinates of the Compton scattering or photoelectric absorption, some minimum energy deposition is required, in order to acquire a sufficiently precise reading from the scintillator's photon sensors. For forward-scattered events, the energy deposition in the scattering layer may not reach that threshold, yielding the transverse coordinates uncertain. In PET-scanning mode, this implies that the coordinates of (at least) one side of the line-of-response (LOR) is uncertain. In this case, it would be advantageous to instead use the coordinates of the absorption event, since that will carry most of the original energy. If the scatter and absorption occurs in scintillator plates that are radially sufficiently adjacent, it is possible to instead use the coordinates of the absorption event as the endpoint of the LOR (given that the scattering angle was small, and the drift length between Compton scatter and absorption short).

FIG. 6b, FIG. 10, FIG. 12a to FIG. 12c, FIG. 14b illustrate examples of a detection module 14 where one or more scintillator plates 16 facing the object (target) is/are separated by a radial gap 17 from one or more other scintillator plates 16. The plates closest to the target form the "scattering layers". By introducing a radial gap to the other layers, the angular resolution is improved. The length of the radial gap H may be tailored to optimize the contradicting constraints of bringing the PET-layers as close together as possible (for compactness and imaging reconstruction accuracy) and to the target as possible, while maximizing angular resolution.

3-Stage Compton Camera

In a variant of the invention, at least one module may also be configured to additionally function as a 3-stage Compton camera, which requires at least 2 radial gaps (i.e. at least 3 radially separated sensor plates).

Cost Considerations, Photon Sensors

Figure 39:
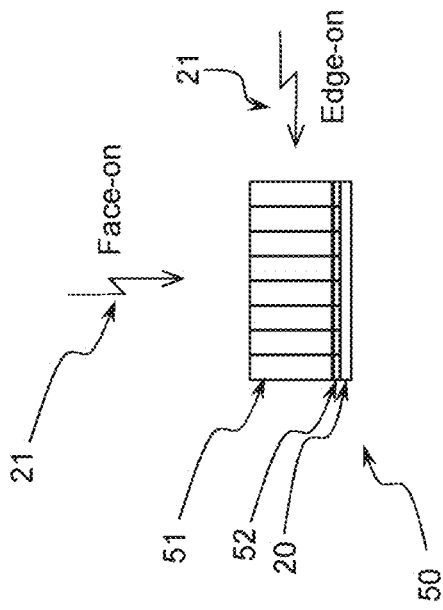
FIG. 39 illustrates a prior art face-coupled detection module with arrays of scintillation crystals and photon sensors.

In a conventional PET-scanner comprising major-face coupled, face-on detection modules (FIG. 39), the total area of photon sensors for a scintillator block or assembly of individual scintillator rods or pixels is approximately equal to $L^2$, L being the length of the scintillator unit orthogonal to the radial direction. With a square edge-coupled detector, the total area of photon sensors is 4LT, T being the radial scintillator thickness. For the area of the edge-coupled photon sensors to be lower than the area of the major-face coupled photon sensors, it is required that L>4T.

With a conventional radial scintillator thickness of approximately 20 mm, the side L would need to be at least 80 mm for the photon sensor area to be equal or lower.

Count Rate Considerations

In particular for range verification applications, the rate of emitted prompt gamma rays may be very high. As an example: at a high therapeutic proton rate of 1.2E10 protons/s, the rate of prompt gammas will be in the order of 1E9/s (Rohling 2017). At a radial distance of 30 cm, this corresponds to about 0.1 gammas/cm2/microsecond, or approximately 2-2.5 gammas per microsecond for a 5 cm×5 cm square detection module. Care should then be taken to ensure that the detector is not saturated or blinded by the high instantaneous rate of gamma rays. Events where the deposited energy does not match a prompt gamma peak of interest may be rejected, in order to increase the ability to distinguish between a gamma ray being Compton scattered from one layer to another, and two independent gamma rays being simultaneously detected in two layers.

Embodiments of the invention include different configurations which allow tailoring the detection module to the expected count rate.

Configuration 1—Independent Layers with Pixel Detectors

In the first configuration as illustrated in FIG. 11b, FIG. 11c, each scintillator plate is equipped with separate photon sensors along the edges. This allows measuring the transverse position and energy of a photoelectrically absorbed gamma ray in one layer, or of a gamma ray that is Compton scattered in one layer and absorbed in another. A second Compton scattering in the second layer would of course also be possible, as well as other interactions, but for brevity we focus here on the aspects of using the invention as a combined single-scattering Compton camera/PET-scanner.

Configuration 2—Strip Detectors Spanning Multiple Layers

In a second configuration (FIG. 11a), some of the photon sensor "pixels" have been replaced with "strips" that span across multiple layers. This has the advantage of reducing the total number of channels and the readout complexity. In order to be able to identify in which layer a scintillating event occurred, each layer is equipped with at least one pixel 18a that can detect scintillating light from that layer only. If the detector functions as a pure PET-scanner, this is a feasible solution. The Compton camera functionality, however, is more difficult to achieve, since the signal read out from one strip would essentially be the sum of two scintillating events in two layers.

Configuration 3—Shared Detectors Strips+Isolated Compton Layer

In a third configuration (FIG. 11d, 11e), one of the layers (16s in FIG. 11d, 16a in FIG. 11e) is optically or electronically or electro-optically separated from the other layers. For Compton camera functionality, this separated layer is used either as absorber portion (16a in FIG. 11e) or scatter portion (16s in FIG. 11d), depending on the primary direction of incoming high energy photons. This layer is used in combination with a stack of scintillating plates, with a photon sensor configuration as described in Configuration 2.

Configuration 4—Split Block

In a fourth configuration (FIG. 12a-12c), the detection module stack of scintillator plates is spatially separated into two portions or blocks 15a, 15s. Each block is arranged as in Configuration 2. Both blocks may be used as a PET-detector. For a Compton camera, one block 15s would be used as a "scatter portion", and the other 15a as "absorber portion".

Configuration 5—Compton Pixel(s)

In a fifth configuration (FIG. 13b), which is primarily intended for high rates of prompt gammas, a single photon sensor 18p (pixel), optically coupled to a scintillating crystal 16p, is used as the Compton absorber (or Compton scatterer), in addition to any of preceding configurations mentioned above. This pixel should be sufficiently small to achieve the desired spatial/angular resolution. This configuration has the advantage that only a small number of additional channels are required to achieve Compton functionality. In variants, multiple individual pixels could be added if necessary. It is also to be understood that this configuration could be "inverted", i.e. that the single pixel 18p, 16p could serve as scattering layer and the scintillator stack as absorber. In either case, the read out chain could be such that only events where the "Compton pixel" is triggered are further processed if the invention operates in Compton mode, discarding all other events.

Configuration 6—Compton Pixel+Compton Layer

Configuration 5 may suffer from count rate saturation if the rate of prompt gammas is very high. To cope with this, Configuration 3 could be modified such that the electronically isolated Compton layer is coupled to a scintillator that may be thinner than the PET-scintillators. The reduced thickness reduces the probability of interaction, which will lower the overall count rate. In addition, the PET-scintillators will absorb part of the prompt gammas, which can further reduce the overall count rate (FIG. 13a).

Inter-Module Compton Camera

Compton camera functionality can also be achieved via inter-module scattering. One detection module 14a acts as scatterer, and another detection module 14b, e.g. a neighboring module, acts as absorber (FIG. 14a, 14b). In this configuration, separate layers for identifying Compton scattered events are not required, and hardware changes with respect to a pure PET-scanner are minimal. Identification of Compton-scattered events can be made for example via total energy discrimination and inter-module coincidence timing. In the gamma energy primarily of interest for proton range verification—a few or several MeV—forward scattering is dominant, and it would be advantageous to introduce a spatial gap 17 between two or several layers 16 in order to improve angular resolution and increase the probability of inter-module Compton scattering.

A conventional PET-scanner calls for a circular assembly to ensure that most of the gamma rays enter the scintillating crystal elements largely perpendicular to the crystal face facing the source. Off-center emission, however, may result in parallax errors. The depth-of-interaction capability of the invention alleviates this problem. Furthermore, the inventors have realized that the depth-of-interaction capability can be exploited in favor of a non-circular assembly (for instance by having a hexagonal assembly as illustrated in FIG. 5a), in order to increase the probability of forward-scattering across neighbor modules. The invention also permits for positioning of sensor plates closer to the patient, or in the direct vicinity of the scanning object.

In another embodiment, as illustrated in FIG. 5b, modules may be arranged in a radially staggered pattern, which also serves to increase the probability of inter-module Compton scattering. In such an arrangement, there would be less need to introduce a radial gap between scintillator plates inside each module.

In another embodiment, as illustrated in FIG. 15a, the detection modules 14s, 14a themselves are arranged in radial groups. The inner group 14s, closest to the source (target), would serve as PET-modules and scatter modules. The outer group 14a would serve as absorber modules for Compton imaging. In FIG. 15a, an example of a nine to one module arrangement is shown, where one single absorber detection module 14a is radially offset and centered over 3×3 PET/scatter detection modules 14s. It is to be understood that other arrangements and ratios between scattering/absorber modules are of course possible, such as 1:1, 9:4 (as shown in FIG. 15b) and others.

The solution of using substantially identical modules as both scatterers and absorbers, optionally radially separated, and optionally with different scintillators thicknesses, has the advantages of simplifying manufacturing and read-out electronics.

Sensor Plate Deactivation

With cross-wire readout (FIG. 19a-19c), or photon sensor strips 18b shared between layers 16 (FIG. 17a-17e, FIG. 18), blocking the scintillation light from one or several layers 16 is possible in order to ensure that the column signals originate from one layer only. This could be achieved by mechanical shutters surrounding the edges of each layer. Another option is to use an electro-optical shutter 24 (FIG. 20a-20c), such as polarizing liquid crystals or transflectors, which can switch between transmissive state 24a and absorbing/reflective state 24b using a drive voltage. In the transmissive state, an electro-optical shutter could also serve as optical spreader between the scintillator 16 and the photon sensors 18.

In an advantageous embodiment, an alternative means to achieve a similar functionality is to selectively enable or disable the photon sensor bias voltage of individual or groups of photon sensors, for example grouped by sensor plate as illustrated via the bias switch network in FIG. 7. Alternatively or additionally, the bias voltage may be adjustable such that the gain of individual photon sensors, groups of photon sensors, a group of photon sensors optically coupled to the scintillator plate, or groups of sensor plates, may be adjustable in accordance to the expected primary gamma ray energies of interest.

Another alternative is to use digital silicon photomultipliers as photon sensors, with which it would be possible to enable/disable individual microcells of the strip photon sensors in order to mask (ignore) the light originating from selected scintillator plates.

Readout Chain

As an alternative to detector strips that are shared between layers, one could instead use individual pixels along the sides of each scintillator block, and a multiplexed readout chain.

A first row/column-readout (crosswire) example for a PET-scanner module is shown in FIG. 19a, where there are 5 square scintillator plates and 5 photon sensor columns per side. In total, the 100 photon sensors can be read via 25 channels. The channels $Y_1$-$Y_5$, corresponding to the sum of layers 1-5, provide information on in which layer(s) the scintillation event occurred. Readout electronics can be further simplified by using these channels as, for example, signal amplitude threshold triggers to assess whether or not a scintillation event occurred in each layer. The PET-scanning data processing circuitry would then only further process events where exactly one layer is involved, ensuring that the column sum signals, $X_1, \ldots, X_N$, correspond to the light emission within one layer only.

A second row/column-readout (cross-wire) example for a combined PET-scanner and Compton camera module is shown in FIG. 19b, 19c, where there are four square scintillator plates and five photon sensor columns per side. In total, the eighty photon sensors can be read out via twenty-four channels. The channels $Y_1$ to $Y_4$ in FIG. 19b provide information on in which layer(s) the scintillation event occurred, and energy (total amount of light). Energy rejection/filtering can be achieved with discriminators. In the embodiment of FIG. 19b, one layer 16a has been spatially separated from the other layers to function as a Compton-absorber layer. The channels $Z_1$ to $Z_{20}$ of the photon sensors of this layer are read out separately. The Compton-camera data processing circuitry will only process events where exactly two layers are involved, one of which being the absorber layer. In this example, 44 channels are required.

Other multiplexing schemes could be used, e.g. symmetric charge division.

Another possibility is to use aggregated quantities of information from the edges of the scintillator plates. One example is to use the center-of-gravity and (charge) sum of each edge. If reducing the number of readout channels, and/or digitizers has a high priority, this could for example be implemented with a resistive network/ASICs prior to digitization as a sum and weighted sum of the pixels along each edge. The output from edge i, based on the N photon sensor columns is then reduced to two quantities per scintillator edge.

$$\{X_1, \ldots X_N\}_i \rightarrow S_{tot,i}, S_{weighted,i}$$

$S_{tot,i} = \Sigma_j^N X_j$ (total sum)
$S_{weighted,i} = \Sigma_j^N \lambda_j X_j$ (weighted sum)

To implement a center-of-gravity algorithm, the weighting coefficients may be equidistantly spaced (assuming all photon sensors have the same length along the edges), e.g. $\lambda_j = j$ $$cog_i = \frac{\sum_{j=1}^{j=N} X_j \times j}{\sum_{j=1}^{j=N} X_j} = \frac{S_{weighted,i}}{S_{tot,i}}$$

The original coordinates of the scintillating event could then be reconstructed, based on the center-of-gravity edge measurements, for example using a calibration table consisting of measured values of $cog_i$ vs. known scintillation event coordinates from a collimated gamma source. The total energy of the event is given by the sum of $S_{tot,i}$ over all edges.

It may be noted that, alternatively or additionally, other aggregates than center-of-gravity could be used, such as index of strip with largest number of counts, truncated center-of-gravity (discarding strips with few counts), full width at half-maximum, skew, or more complex functions.

The technique of using aggregated edge-quantities for event reconstruction could either be implemented in an analog manner (prior to digitization), using e.g. resistive charge division circuits (CDC), or after digitization with the purpose of speeding up image reconstruction methods by reducing the dimensionality of the data set per scintillating event.

Layer Identification Based on Time-Difference of Dual-End Strip Detectors

Another method of layer identification is to read out the strip photon sensors 18 at both ends 41a, 41b as illustrated in FIG. 18. Such a dual readout of a strip silicon photomultiplier is per se known and described in e.g. Doroud 2017 [11] (using differential readout for noise suppression), reporting that the propagation speed of the signal across the strip is approximately $v_{prop} \approx 1E7$ m/s. The difference in arrival time of the pulse to the two ends, upper (subscript u) and lower (subscript l) is:

$$\Delta T = t_u - t_l = 2 \times \frac{z}{v_{prop}}$$

where z is the distance between the scintillating layer and the middle layer (i.e. zero if the scintillation occurs in the middle layer). With a scintillator plate thickness of e.g. 3 mm, the difference in $\Delta T$ between two neighboring layers is about 200 ps (picoseconds), which is measurable using state-of-the-art readout technology. Furthermore, since the light from any scintillating event will be distributed over multiple strips along the edges, the layer resolution can be improved by taking the time difference of several strips into account for identifying the layer (e.g. by averaging the time difference of all strips, or all strips with a signal amplitude above a threshold). This method has the advantage that the layer-identifying photon sensors 18a can be replaced with strip detectors 18b, significantly reducing the total number of channels. The number of layers, and, consequently, the depth-of-interaction resolution, is mainly limited by the timing precision.

System Assembly

FIG. 16a shows a dual-head assembly, and FIG. 16b a triple head assembly, in a proton therapy setting. In the dual-head assembly the ion beam 1 enters a target in the y-direction, and two detector assemblies 13a, 13b are arranged around the target 4 symmetrically in the ±z-direction. The two assemblies 13a, 13b will intercept a fraction of the gamma rays emitted along the proton beam path: prompt gamma rays 21b and positron-electron annihilation gamma rays 21a. In the triple head assembly, an additional detector assembly 13c is arranged around the target facing substantially the proton beam emitter.

Layer Identifying Pixels—Configuration

In a configuration where all but one column of the photon sensors are shared across two or more layers 16, a sufficient amount of light should reach the pixels 18a that are used to identify in which layer the scintillating event occurred. As illustrated in FIG. 17a to FIG. 17e, these pixels 18a could be located at the corners, at the center of the edges, or somewhere in between.

FIG. 21b displays a contour map of the number of photons reaching the pixels, as a function of the transverse coordinates of the scintillating event, using rather conservative assumptions on the crystal light yield (30,000 photons/MeV, gamma energy=511 keV) and the photon sensor parameters (Photon Detection Efficiency=0.2, Dark count rate=130,000 Hz/mm2, Excess Noise Function=0.2, signal integration time=250 ns). In these figures, it is assumed that each edge is equipped with 5 photon sensors (20 in total) as illustrated in FIG. 21a. The plots show the light received for a single 10 mm wide photon sensor located on the right edge (x=25), from bottom to top (y=−25 to y=+25). For the photon sensors located along the other edges, the situation is rotationally symmetric. The photon sensor located close to the lower corner receives very little light for events originating close to the right edge (x~25 mm, y>−15 mm), and at the top right quadrant. The photon sensor located at the center of the edge receives about 50 or more photons for all events originating on the left side (x<=0), but few photons for events originating around the upper left corners. Note that >50 photons are a mean value of the simulated events. Events with more or fewer detected photons will occur. However, even when taking into account statistical fluctuations, this level is fully sufficient to yield a signal that is well above the noise floor and estimated dark count rate.

Figure 17A:
FIG. 17a illustrates a photon sensor arrangement with photon strip detectors of a detection module according to an embodiment of the invention.
Figure 17B:
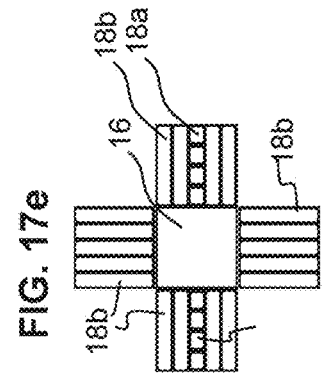
FIGS. 17b to 17e illustrate the arrangement of photon sensors on four sides of the scintillator plate stack with both individual and strip photon sensors according to different variants.
Figure 17C:
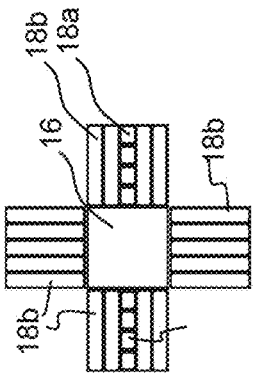
Figure 17D:
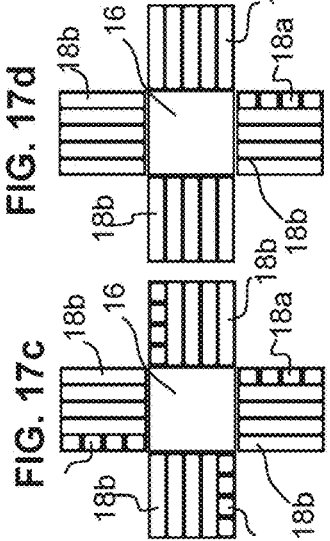
Figure 17E:
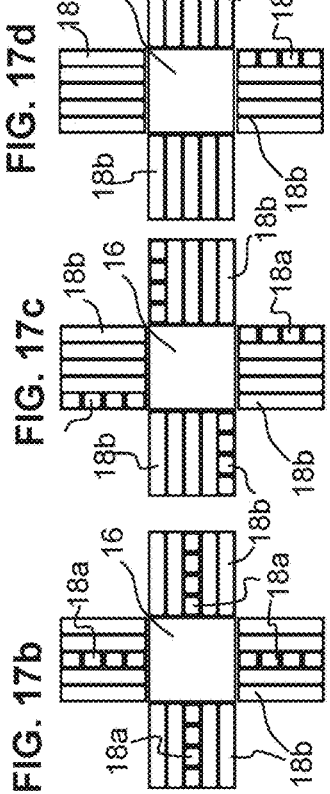

Thus, in order to reliably determine in which layer an event occurred, it would be sufficient to position two layer identifying photon sensors at the center of two opposing edges only as illustrated in FIG. 17e. By considering the sum of the two pixels, or only the pixel with the largest signal amplitude or integral, one could reliably identify the layer of the scintillating event. A 4-layer square detection module, 5 detector columns on two opposing edges, as illustrated in FIG. 17e, would in this case require only 26 channels.

Detector Geometry and Pixel Configuration

The geometry of a monolithic detection module in terms of shape, area and photon sensor configuration affects performance. Different polygon shapes of the front and back faces, as well as different number of photon sensors per edge have thus been simulated. For each simulation scenario, a large number of events were simulated, each event being isotropic photon emission from a scintillating event in a randomly chosen point ($x_0$, $y_0$, $z_0$) within the scintillator bulk, ray tracing in the crystal and spreader material, as well as the response (number of photons detected) of individual photon sensors. As mentioned above, conservative manufacturer figures of dark count rate, excess noise etc. were used to estimate the response of the photon sensors, taking statistical fluctuations into account.

The photon sensor responses from a large number of events were used to estimate the mean and standard variation of the detectors as a function of transverse coordinates $x_0$ and $y_0$ within the scintillator. This is the training set, or calibration set. The depth, $z_0$, was not part of the calibration set. Then, another set of events was used as evaluation set, where it was investigated how well a backtracking algorithm could predict the original transverse coordinates, $x_0$, $y_0$ of the scintillating event based on the training set. The predicted, or fitted, coordinates are denoted $x_{fit}$, $y_{fit}$. The transverse error $\varepsilon$ was then calculated as the Euclidian distance:

$$\varepsilon = \sqrt{(x_{fit}-x_0)^2 + (y_{fit}-x_0)^2}$$

For the entire evaluation set, one can then calculate the mean error $\bar{\varepsilon}$.

The mean error itself is not a useful metric of whether the monolithic edge detector is a better choice than a conventional PET-scanner configuration. In order to reduce the mean error of a conventional PET-scanner, one could simply reduce the dimensions of the scintillator crystals and the photon sensors, and increase the number of scintillators and detectors.

As a comparative metric, the inventors chose to compare the number of photon sensors of the invention, with the number of photon sensors of a "conventional PET-scanner" with a similar transverse total area and a similar spatial resolution (same mean error). The conventional PET-scanner was defined as:

Individual scintillating crystals (rods), square shaped, 1-to-1face-coupled to individual photon sensors.

Figure 22:
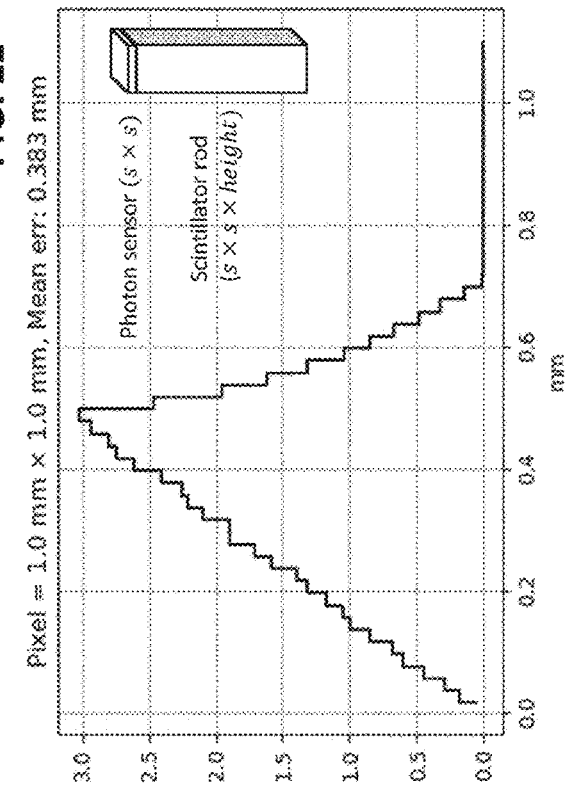
FIG. 22 is a plot illustrating the distribution of errors in a conventional PET scanner using photon sensors each having a receiving surface area of 1×1 mm.

To estimate the mean error of a conventional configuration, a simulation was made resulting in the error distribution illustrated in FIG. 22. Since a single pixel crystal does not yield any information on where in the single crystal the scintillating event occurred, the transverse coordinates of each event were assigned to the center of the crystal. The maximum error would occur for events originating at the corner of the crystal. The mean error is approximately equal to:

$$\bar{\varepsilon}_{conv} \approx 0.38 \times s$$

Where s is the side of the crystal element face toward the source. Setting $\bar{\varepsilon}_{conv}$ equal to the mean error of embodiments of the invention, we get the crystal dimensions:

$$s = \frac{\bar{\varepsilon}}{0.38}$$

from which the total number of channels of a given total transverse area can be calculated. A typical example of a conventional PET-scanner configuration could be scintillating crystals with dimensions of 3.1 mm×3.1 mm×20 mm (3.1 mm in X and Y, 20 mm in Z), coupled to a SiPM array with SiPM pixels having dimensions of 3.3 mm×3.3 mm. The fill factor of such a configuration would be around 88%, not taking into account gaps between modules.

A monolithic detector was evaluated, the detector having a transverse surface area of 2500 mm$^2$, surrounded by a 4 mm non-scintillating frame-like gap in order to account for optical spreader and space for photon sensors. The fill factor for such a detector is:

Triangular shape: 72% (FIG. 9c)
Square shape: 74% (FIG. 9a)
Hexagonal shape: 76% (FIG. 9b)

Overall, when taking into account non-scintillating gaps between modules, we consider the fill factor of a conventional PET-scanner to be similar to the fill factor of embodiments of the invention.

Figures 24, 25, 26:
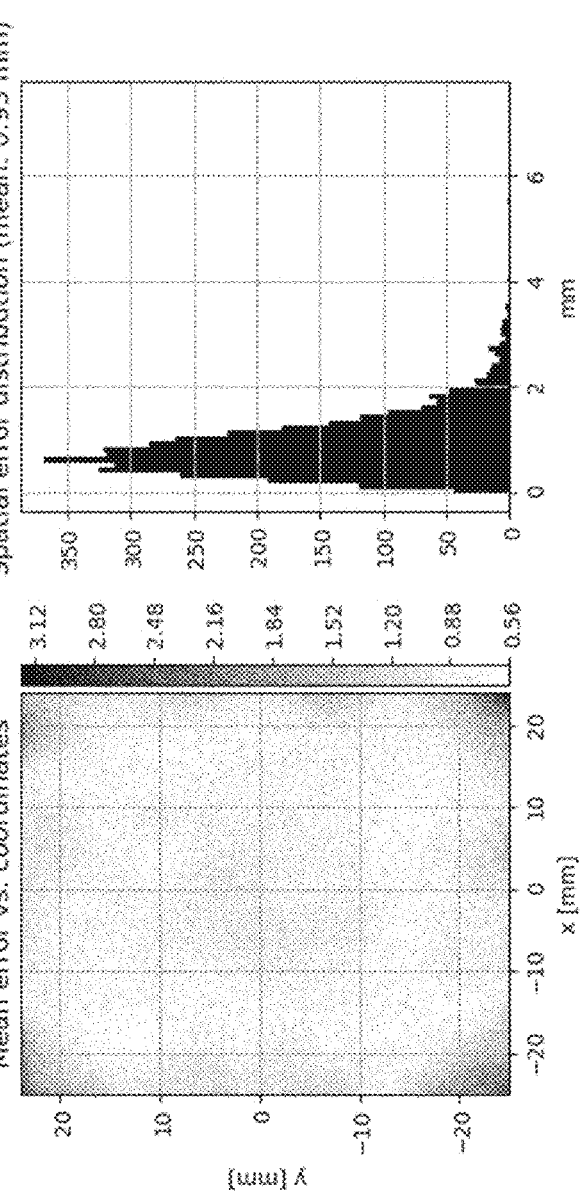
FIGS. 24 to 26 are plots illustrating the spatial precision of embodiments of the invention.

FIG. 24 illustrates an example of the true vs. reconstructed interaction position in a 50×50 mm scintillator plate, generated from simulations. FIG. 25 illustrates the mean transverse (axial-azimuthal) spatial reconstruction error across the scintillator plate, whereas FIG. 26 is a histogram of the mean transverse reconstruction position error. In this example, a mean transverse error of 0.93 mm was achieved.

Embodiments of the invention allow for increasing the effective thickness of scintillating material by adding more layers, without significant degradation of image quality. A somewhat lower fill factor, compared to a conventional PET-scanner could thus be compensated by an increase in coincidence probability from more scintillating material.

One may define the optimization metric of embodiments of the invention as the ratio between the number of channels of a conventional PET-scanner, to the ratio of number of channels for a single layer of the device:

$$R = \frac{N_{ch}}{N_{ch,conv}}$$

Figure 23:
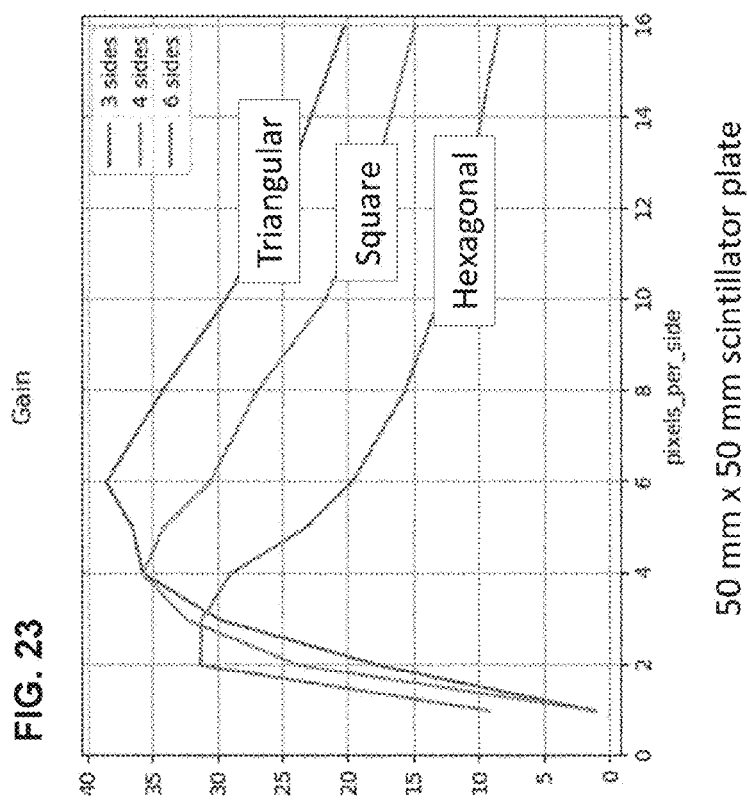
FIG. 23 is a plot illustrating the ratio between the number of photon sensors of a conventional PET scanner and the invention, versus the number of photon sensors (i.e. called "pixels") per edge, for triangular (FIG. 9c), square (FIG. 9a) and hexagonal (FIG. 9b) shaped scintillator plates having respectively three, four and six sides.

FIG. 23 shows the ratio R for triangular, square and hexagonal scintillator plates, versus the number of photon sensors per edge. A square detector may be simplest to manufacture, and the optimum number of pixels per side is then 5, although a similar gain can be achieved with 4 or 6 photon sensors per side. The ratio R would be lower if considering a conventional PET-scanner where a photon sensor array of M×M detectors is coupled to a crystal array of N×N crystals, N>M, with e.g. a monolithic light guide inserted between the crystals and the photon sensors. A 4×4 detector array coupled to a 5×5 crystal array would reduce our R by 36%. Obviously, the ratio R will also be lower if the number of layers is increased. However, this metric does not take into account the gain in DOI. If DOI-information is not needed (e.g. the thickness of the scintillator plate is the same as the height of an individual crystal of a conventional PET-scanner), then R is valid.

In general, for triangular, square or hexagonal shapes, one could achieve a reduction of the number of channels by a factor 30 to 40, compared to a 1-to-1 coupled conventional PET-scanner. This is a significant improvement, which significantly reduces the cost of the PET-scanner. Alternatively, the gain in reduced number of channels could be exploited to instead increase, in particular, the PET-scanner's axial Field Of View (FOV). This would be particularly advantageous for total Body PET-scanner applications, where the axial FOV may span the entire patient.

Compton Camera Scintillator Plate Thickness Optimization

The probability of a valid Compton scattering event (Compton scattering in one scintillator plate, photoelectric absorption in another scintillator plate) occurring generally depends on the thickness of the scintillator plates. A detailed study of this probability, involving different primary gamma ray energies and total radial scintillator thickness was made for a 2-layer configuration, with varying scatter and absorber scintillator thicknesses, as summarized in FIG. 34. For lower energies (0.511 keV), the optimal ratio is in the range 30%-50%, depending on the total scintillator thickness (6-20 mm). However, for higher energies, the optimal ratio is closer to 50%, i.e. equal thickness of the scatterer and absorber. Depending on the variant, and energy of interest, a scatter layer thickness between 20% to 60% of the total thickness is preferred.

Calibration—Reference Table

A calibration of the detection system may advantageously comprise the following steps:
  Irradiating the detector with a collimated source at known transverse coordinates ($x_{cal}$, $y_{cal}$) The depth of interaction, $z_{cal}$, does not need to be precisely known.
  Recording a sufficiently large number of event per detector layer and calibration position
  Calculating the mean and standard deviation of the response of each photon sensor i at a given position, $\mu_i(x, y)$ and $\sigma_i(x, y)$.
    A reference table may be generated from the calibration positions, and, optionally, fine-grid interpolation of the mean and standard deviations of each photon sensor at any intermediate positions not part of the calibration procedure.

One could alternatively 1 in addition to $\mu_i$ and $\sigma_i$ of individual photon sensors also calculate any aggregate quantities (such as center-of-gravity).

Event Reconstruction

To reconstruct the interaction coordinates of a single event, the following method could be employed:
  Digitization of photon sensor responses, and/or aggregate quantities
  Find the position in the calibration table that best matches response (various per se known methods could be used to do this efficiently).

Event Rejection

In both PET-scanning mode and Compton camera mode, rejecting events based on energy deposition is advantageous. In addition, rejection of double- or multi-scattering events in the same scintillator is also advantageous. One method is to compare the event signature (signal per readout channel) to its closest match in the reference table. "Closest match" implies e.g. the standard deviation-normalized Euclidian distance (sum of squared differences, divided by the standard deviation of the pixel response or aggregate) between the event and the closest reference match. If this difference is larger than a configurable threshold value, the event may be rejected.

PET-Scanning Mode Vs. Compton Camera Mode

When the detector assembly operates in PET-scanning mode, only events where two sensor plates opposite from the source are triggered (i.e. along the LOR) shall be considered. In a proton therapy context, due to the potentially high trigger rate from prompt gamma rays during proton delivery, PET-scanning mode may optionally be completely disabled while the ion beam is being delivered. Since the imaging volume of interest (defined by the treatment volume and the proton beam path), is well defined (within uncertainty margins), valid coincidence groups of detection modules could be defined to discard any coincidence events outside the imaging volume of interest. In addition, one or multiple energy windows may be defined to reject events not corresponding to gamma energies of interest.

In Compton Camera mode, one could accept, for example, only events where two layers within one module (intra-module Compton Camera) are triggered or single layers in two nearby modules (intra-module Compton Camera). Multiple energy rejection windows (where the energy is the sum of the signal from the two triggered layers) could be defined in order to accept only events corresponding to known prompt gamma emission peaks. To further limit data rate, one could enable only modules where the image reconstruction resolution is highest in the direction of the proton beam, if one is primarily interested in the proton beam range in the target.

Multiplexed Readout of Azimuthally-Axially Arranged Sensor Plates

A major disadvantage with the previously disclosed arrangements, where radially stacked blocks are read out in a multiplexed manner, or via strip sensors, is that they are inefficient for detection of forward Compton scattered gamma rays. Gamma rays being forward-scattered are likely to either interact either in a single sensor plate (if the scattered gamma ray is not detected), or in two sensor plates that are generally radially aligned. It would in most cases not be possible to separately reconstruct the two interaction positions. Only if the Compton scattering is such that the two interactions occur in two separate modules ("inter-module scattering", low probability), or if additional scattering/absorption sensor plates or Compton pixels with independent photon sensors are added (increased complexity) would it be possible to reconstruct the two interaction positions. In particular at energies of interest for detection of Prompt Gamma Rays (up to 7 MeV), small angle forward scattering is dominant.

In order to overcome the inherent disadvantages of combined readout of a radially stacked multi-layer configuration, a novel multiplexed readout scheme is introduced. Rather than combining the signals from compactly arranged and radially stacked sensor plates, into common readout channels (with previously discussed drawbacks), the inventors have realized that it would bring significant functional and performance advantages to arrange common readout sensor plates in a radial plane, rather than in a radial stack. By arranging common read-out scintillator slabs azimuthally-axially, rather than radially, one overcomes several disadvantages. An illustration of azimuthally-axially arranged sensor plates is shown in FIG. 28.

The terminology radially-azimuthally-axially herein refers to the common cylindrical arrangement of a PET-scanner's scintillator elements. Other arrangements, to which the cylindrical coordinate system terminology is not directly applicable, are possible, such as spherical, "box-like", dual-head (FIG. 5e), quad-head (FIG. 5f) or helmet-like (e.g. for a dedicated brain PET-scanner). They all, however, have in common that the scintillator elements are arranged around the volume of interest in some fashion.).

One example of a multiplexed read-out configuration is illustrated in FIG. 29 for a 2×2-sensor plate in an azimuthal-axial configuration. Each sensor plate has a plurality of photon sensors, for instance 8 photon sensors 18. Depending on the configuration, the multiplexing circuits 33 may implement an analog sum of the connected photon sensors 18. This would allow for reading out the sum of each sensor plate individually, S1-S4, as well as, for example, the sum of all photon sensors at a particular location on the sensor plates ("upper right", "upper left", etc.), E1-E8. The sum circuits S1-S4 allows identifying in which scintillator plate 18 a scintillating event occurred, while E1-E8 may provide spatial information on the scintillating event.

By multiplexing the photon sensor signals from azimuthally-axially arranged blocks, all benefits in terms of reducing the number of readout channels are preserved. Advantageously, the scheme also allows for independent readout of radially separated layers. The azimuthal-axial multiplexing arrangement is particularly well suited for resolving Compton scattered 511 keV gamma rays from electron-positron annihilation. If the layers are sufficiently thin, it is unlikely that a single 511 keV gamma ray will be both Compton scattered and absorbed in the same sensor plate. This advantage is particularly important since it allows for accepting a larger fraction of incoming 511 keV gamma rays. In a conventional PET-scanners, one typically only accepts events with a deposition energy of 511 keV (within an instrumental energy acceptance window), in order to reject Compton scattered gamma rays, and only accept events where the 511 keV gamma ray is directly photoelectrically absorbed. One of the reasons being that a conventionally pixelated PET-scanner does not have depth-of-interaction resolution, and the initial interaction position cannot be unambiguously determined. However, in the present invention, it is possible to determine both scatter and absorption coordinates. Depending on the gamma ray energy of interest, Compton kinematic rules may be applied to resolve in which scintillator plate the scattering occurred, and in which plate the absorption occurred. The temporal sequence may also be determined via timestamps. If the temporal sequence cannot be unambiguously determined, probability-weighted LORs (PET) or Compton-cones (Compton camera imaging) may be used for the image reconstruction. Prior knowledge on the spatial origin of the primary gamma rays may also be exploited to accept or reject LORs or Compton-cones.

In general, the feature of being able to resolve also Compton scattered gamma rays in PET-scanning operation will significantly increase the overall detector sensitivity: the fraction of coincidentally detected 511 keV gamma rays.

As an example: consider a configuration where the total radial scintillator thickness is 20 mm (for example LYSO), divided into 5 azimuthally-axially stacked modules of 4 mm thickness. The probability that a 511 keV gamma ray impending on the arrangement will interact in some way is about 80%. However, the probability that it will be directly photoelectrically absorbed is only 26%. The probability of simultaneous photoelectric absorption of two coincident, anti-parallel, gamma rays is thus only 0.26*0.26=6.7%. This fundamentally limits the sensitivity of a conventional PET-scanner.

To compare with the inventors' azimuthally-axially multiplexed sensor plates, we assume that, for example, events where E1>100 keV and E2>100 keV can be unambiguously resolved. In addition to directly photoelectrically absorbed event, the probability of a 511 keV gamma ray to be first Compton scattered, followed by photoelectric absorption in a radially different layer is 11.4%. The probability of detecting a 511 keV gamma ray either via direct photoelectric absorption, or as a two-stage Compton event (scattering+absorption) is thus 26%+11.4%=37.4%. The probability of coincident detection is $0.374^2$=14%.

Thus, embodiments of the invention may have an overall sensitivity, or valid coincidence detection rate, that is approximately a factor of 2 higher than a conventional detector. Half the number of emitted gamma rays is required to form an image of equivalent quality. Or, alternatively, in a radiopharmaceutical context, the injected tracer isotope could be significantly reduced in order to minimize the patient exposure dose.

Combined Signal Readout of Edge-Adjacent Photon Sensors

Figure 40:
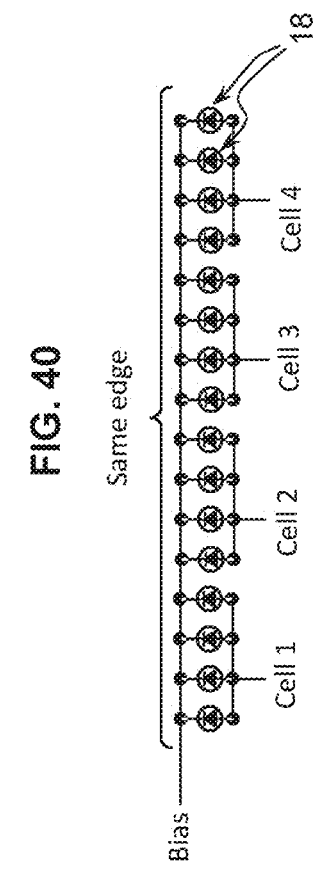
FIG. 40 illustrates a 16:4 multiplexing variant (common anode) of photon sensors along the same edge, whereby the current sum of adjacent photon sensors may be read out according to an embodiment of the invention.

Commonly available photon sensors, such as silicon photomultipliers are typically square shaped, for instance 1×1, 3×3, 4×4 or 6×6 mm, to which the precise dimensions of the invention's scintillator plates may be adapted. In a variant, the desired scintillator plate dimensions may be for instance 48×48×3 mm (3 mm being the radial thickness). To match the radial thickness, 3×3 mm photon sensors would be suitable. In a variant of the invention, the number of photon sensors per edge should be at least 2, at least 3, at least 4, at least 5, at least 6, at least 7 or at least 8. However, 3×3 mm photon sensors would be equivalent to 16 channels per edge. In an advantageous embodiment of the invention, the signal from adjacent photon sensors may be added electronically, such that groups of adjacent photon sensors are read out as one, or connected to the multiplexing circuits as one, prior to digitization. FIG. 40 illustrates an example of a 4:1 reduction of the number of channels per edge, using common-anode current summation. Other signal summation techniques are per se known, addressing issues such as increased effective sensor capacitance, and may be used in embodiments of the invention.

Axial Field of View Extension

Figure 38:
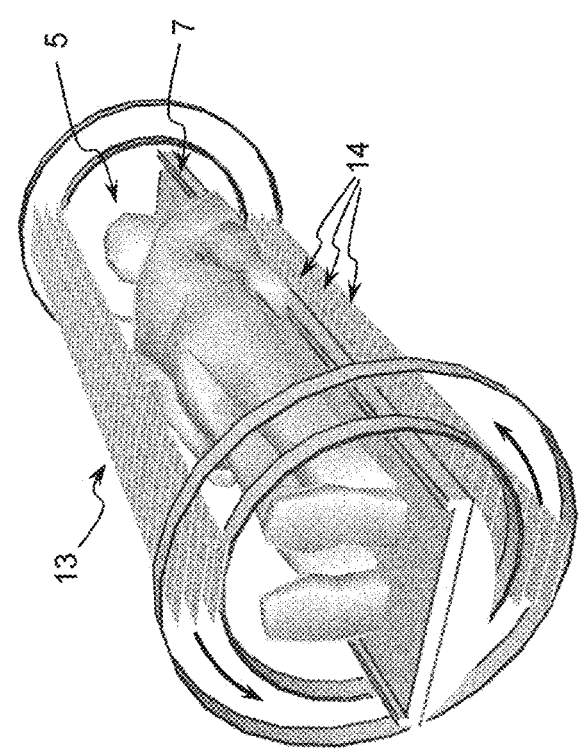
FIG. 38 illustrates a variant of a total body scanner (PET or Compton-PET, depending on the configuration) in a rotating dual-head configuration with two radial gaps according to an embodiment of the invention.

In an advantageous embodiment, at least two azimuthally opposing sensor plate arrangements may rotate around a patient or scanning object to acquire partial or total body PET and/or SPECT imaging, as illustrated in FIG. 38. The detector may be combined with CT-imaging equipment. The detector may be combined with an MRI. The detector may acquire dynamic images ("4D"-images with volumetric and temporal information).

Figure 32:
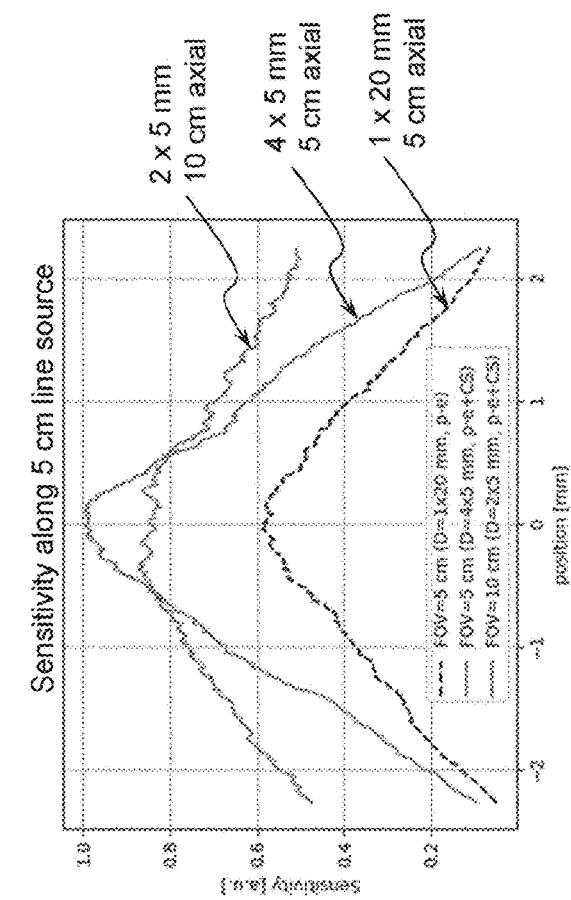
FIG. 32 is a schematic illustration of the detector sensitivity along an axial line source, for different sensor plate arrangements.
Figure 31:
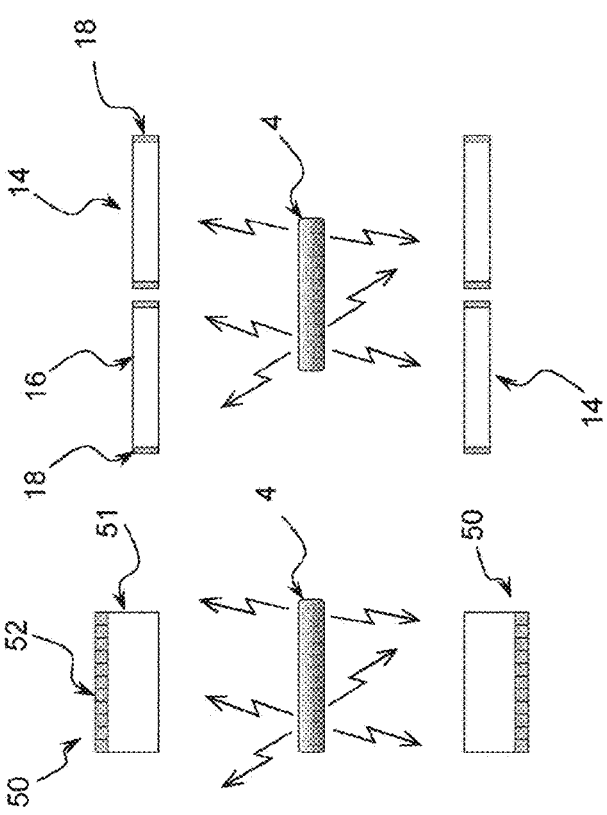
FIG. 31 is a schematic illustration of an advantageous arrangement of embodiments of the invention for achieving an extended axial Field-of-view, compared to a conventional detection module.

A major limitation of most conventional PET-scanners is the limited axial FOV. Manufacturing costs generally increase linearly with extended FOV, as more photons sensors, readout channels and scintillator material must be added. Costs could be partially reduced by decreasing the radial scintillator thickness, but this does not reduce the scintillator area that must be covered with photon sensors. As an example, consider a line source with an axial extent similar to that of a conventional PET-scanner, as conceptually illustrated in FIG. 31. In order to coincidentally detect annihilation gamma rays emitted close to the ends of the line source, the scanner or scanning object must be moved axially, prolonging imaging time, and making it challenging to image dynamic processes along the line source. However, the axial FOV of the invention can be increased by simply rearranging the sensor plates in the axial direction, as illustrated in FIG. 30, with no or minimal cost increase. While the total radial scintillator thickness is reduced, decreasing the coincidence probability, this is compensated by an increased FOV. In addition, with an azimuthally-axially multiplexed arrangement, the capability of accepting Compton scattered events significantly increases the overall sensitivity. A comparison of axial sensitivity is illustrated in FIG. 32.

Figure 36:
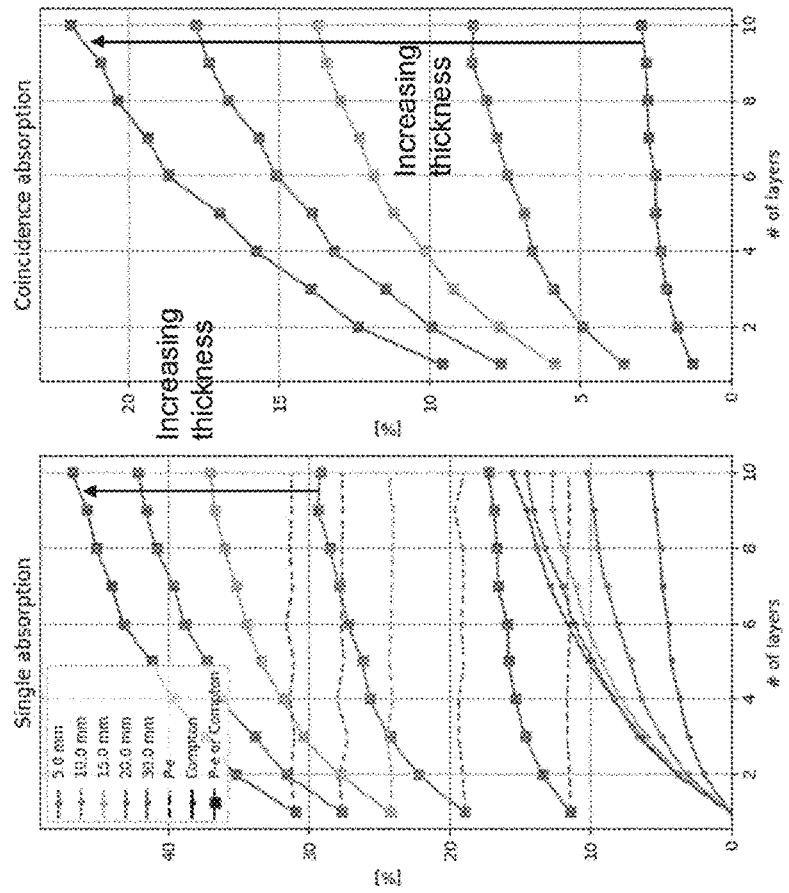
FIG. 36 show plots illustrating the probability of absorbing a primary gamma ray directly via photoelectric absorption ("p-e"), or via single Compton scattering ("Compton"), or the sum of the two ("p-e or Compton"), whereby the left plot illustrates the probability of coincident absorption.

As illustrated in FIG. 36, changing sensor plate configuration from a single radial layer to two or more radial layers may in fact increase the probability of coincidence detection, even if the total scintillator thickness is reduced. For instance, the probability of valid coincidence absorption of a single-layer configuration with 20 mm radial scintillator thickness is similar to the probability of a valid coincidence absorption of a 2-layer configuration with a total thickness of 15 mm, or a 4-6 layer configuration with a total thickness of 10 mm. It is therefore an advantage with the invention that the total scintillator volume—and the total area needed to be covered by photon sensors—may be significantly reduced, thereby reducing overall costs, and/or allowing for an increased axial FOV.

The radial scintillator thickness may be for instance less than 40 mm, less than 30 mm, less than 20 mm, less than 15 mm, or less than 10 mm, distributed over at least two scintillator plates.

In a face-coupled detection module, a radial scintillator thickness of approximately 20 mm is typically considered a cost-effective optimum for PET-scanning, considering the probability of coincidence detection. In an advantageous embodiment of the invention, the radial scintillator thickness may be reduced, for example less than 19 mm, since also Compton scattered gamma rays may be accepted as valid events.

Figure 33:
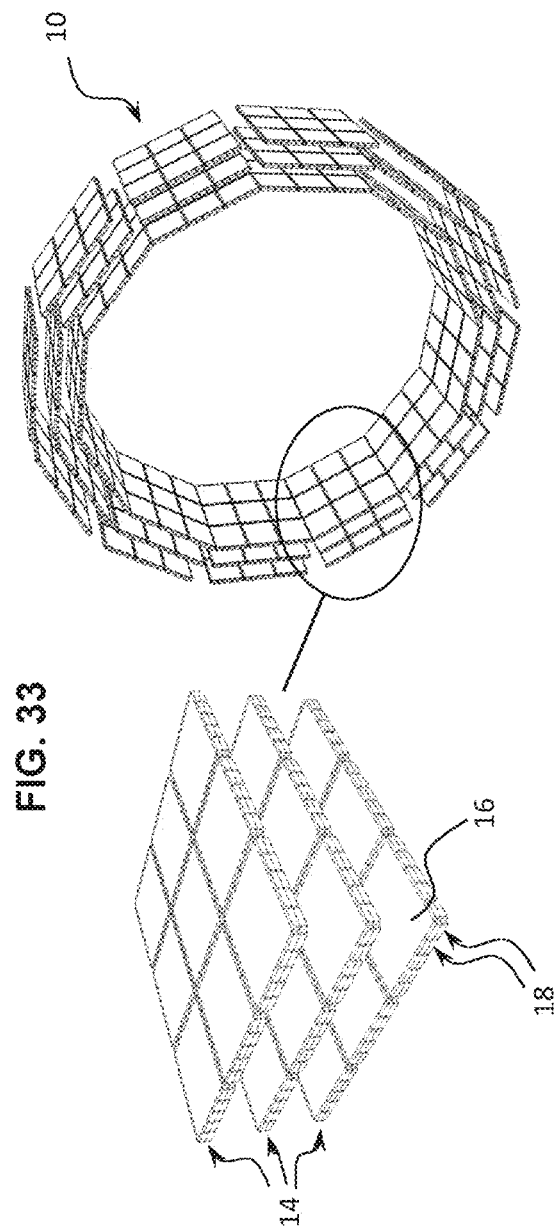
FIG. 33 is a schematic illustration of a ring-shaped assembly of axially-azimuthally arranged sensor plates with 2 radial gaps and 2+2+2 radial layers according to an embodiment of the invention.

In an advantageous embodiment, the azimuthally-axially multiplexed configuration may also be adapted to include more than one radial gap, as illustrated in FIG. 33, showing a configuration with 2+2+2 radially stacked scintillator blocks multiplexed in a 3×3 fashion. Such a configuration could function as a PET-scanner, a 2-stage Compton camera and a 3-stage Compton camera. Radial air gaps between sensor plates may also improve heat dissipation.

The multiplexed sensor plates may, for example, be arranged in azimuthal-axial array in a 1×2, 1×3, 1×4, 2×2, 2×3, 2×4, 3×3, 3×4, 4×4, 4×5, or 5×5 manner.

Feature Combinations and Uses

Features of the different embodiments are exchangeable between the embodiments and may be combined in different ways, unless anything else is specifically indicated. Even though in the following description, numerous specific details are set forth to provide a more thorough understanding of the present invention, it will be apparent to one skilled in the art that the present invention may be practiced without these specific details. The basics and conventional techniques in electronics, sensor systems, image analysis, signal processing, data communication systems, image acquisition systems, and other components to carry out the invention are considered to be readily understood by the skilled person in the art and therefore for the sake of brevity, further explanations and details will be omitted in this description.

The detection system according to embodiments of the invention can also be used for other types of nuclear imaging such as imaging of 3-γ emission, or isotopes that emit one positron (producing coincident, opposing 511 keV γ-s, which, when detected, yield a LOR 27 along which the source is located) and another γ (which yields a Compton-cone 25 on which the source is located). Combining the information from the LOR and the Compton cone makes it possible to triangulate the possible isotope positions to a very high accuracy—in particular in an ion beam therapy context, where the volume of interest is well known, as illustrated in FIG. 27.

In WO 2018/081404 A1, a radially stacked edge-detection detector with individual photon sensors for each layer is disclosed. With a single layer, this reduces the number of channels significantly, compared to a 1-to-1 major face-coupled PET-scanner. The number of channels, however, increase linearly with the number of layers. According to an aspect of the present invention, a combination of strip photon sensors spanning over multiple layers and pixel photon sensors coupled to a single layer, reduces the number of channels significantly even of a multi-layer detector, while at the same time making it possible to identify in which layer a scintillating event occurred via the pixel detectors.

According to another aspect of the invention, dual-ended strip photon sensors are used, whereby the time difference between the two ends is exploited to resolve in which layer the scintillating event occurred. The total number of read-outs then do not depend on the number of layers in a module. This solution has the advantage that layer-specific pixels are not needed. Depth-of-interaction resolution is only limited by timing precision and the number of scintillator plates.

According to another aspect of the invention, the detection system uses neighboring modules as scatterer module/absorber modules of a Compton camera ("Inter-module Compton camera"). Thanks to the depth-of-interaction resolution, this configuration is more robust against parallax errors due to gamma rays entering the detector at an angle. A non-circular arrangement of detection modules—such as hexagonal, octagonal or other multi-polygonal shapes—around the scanning object would therefore increase the probability of detecting forward-scattered gamma rays in two different modules, compared to a conventional circular arrangement.

According to another aspect of the invention, electro-optical shutters for temporarily blocking the optical signal from selected layers is provided. In particular, this is advantageous when the stacked detector is read-out with strip detectors, spanning over multiple layers. The electro-optical shutters could, for example, be used as a means to functionally transform some of the layers that are radially closest to the imaging object into "gamma filters". This is a useful feature in a situation where the instantaneous rate of prompt gamma rays is so high that the detector would saturate, if all layers were optically active. By temporarily blocking light from the layers closest to the target, these proximal layers would serve to absorb a fraction of the prompt gamma rays without blinding the detector. The overall count rate of the detector would then be reduced.

According to another aspect of the invention, an arrangement of conceptually identical modules (each module consisting of scintillator plates, photon sensors and read-out electronics) can be arranged to serve as a combined PET-scanner and Compton camera, where a radially offset group of modules serve as absorbers in a two-stage Compton camera. This configuration is advantageous from a manufacturing and cost perspective, while also being easy to customize.

According to another aspect of the invention, an azimuthal-axial arrangement of sensor plates with multiplexed readout is provided. In particular, this is advantageous for detection of Compton scattered gamma rays for both PET-scanning and Compton camera functionality over a large solid angle around a volume of interest, as well as reducing parallax errors.

PRIOR ART REFERENCES

[1] CN 107544086 A
[2] WO 2018/081404 A1
[3] K. Shimazoe et. al, 2020, Nuclear Inst. and Methods in Physics Research, A: https://doi.orq/10.1016/j.nima.2018.10.177
[4] EP1617237 A1
[5] US 2018/172847 A1
[6] US 2005/116173 A1
[7] Georgy Shakirin et al 2011 Phys. Med. Biol. 56 1281 (Shakirin 2011): https://doi.orq/10.1088/0031-9155/56/5/004
[8] Rohling et al, 2017, Phys. Med. Biol., at press (Rohling 2017): https://doi.orq/10.1088/1361-6560/aa6068
[9] Antje-Christin Knopf and Antony Lomax 2013 Phys. Med. Biol. 58 R131 (Knopf 2013)
[10] January et al, 2017, Med. Phys. 44 (12), December 2017 (January 2017) (https://doi.orq/10.1002/mp.12626)
[11] K. Doroud, M. C. S. Williams, K. Yamamoto (Doroud 2017) The Strip Silicon PhotoMultiplier: An innovation for enhanced time and position measurement, Nuclear Instruments and Methods in Physics Research Section A: Accelerators, Spectrometers, Detectors and Associated Equipment, Volume 853, 2017, Pages 1-8, ISSN 0168-9002,

| List of features referenced in the figures |
| --- |
| Patient 5 |
|   Target zone (e.g. tumor) 4 |
|   Ion beam therapy system 6 (e.g. Proton beam therapy system) |
|     Patient support 7 |
|     Ion beam emitter 8 |
|       Ion beam 1 |
|       Scanning magnets 2 |
|       Beam intensity and profile monitors 3 |
|   Gamma ray detection system 10 |
|     Compton camera 11 |
|     PET scanner 12 |
|     Detection module assembly 13, 13a, 13b, 13c |
|       Opening 42 |
|       Detection modules 14, 14a, 14s |
|         Scatter portion/block 15s |
|         Absorber portion/block 15a |
|         Sensor plate 16, 18 |
|           Scintillator plate 16 |
|             Scatter layer 16s |
|             Absorber layer 16a |
|             Major surface 40a |
|             Lateral minor surfaces 40b (also named "edges") |
|           Scintillator rod 16p |
|           Radial Gap 17 |
|           Photon sensor 18 |
|             Individual layer photon sensor 18a |
|             (also named "photon sensor pixel" or just "pixel") |

| -continued |
| --- |
| List of features referenced in the figures |
|             Photon sensor 18p coupled to scintillator rod 16p |
|             Crosswire connection arrangement 18c |
|             Strip Multilayer photon sensor 18b |
|             (also named "photon sensor strip" or just "strip detector") |
|           Photon sensor support (board) 20 |
|           Detector-scintillator optical interface 22 |
|           Electro-optical shutter (EOS) 24 |
|           Edge light Spreader 26 |
|           Interlayer reflector 28 |
|           Light partial barrier/absorber 29 |
|           Low refractive index gap 31 |
|     Signal processing and control system 30 |
|       Circuit board 32 |
|         Multiplexing circuit 33 |
|         Electronic components 34 (e.g. Microprocessor, Memory, FPGA, etc.) |
|       Connectors 36a, 36b |
|   Gamma ray 21 |
|     Positron gamma ray 21a |
|     Prompt gamma ray 21b |
|   Source 23 |
|   Compton cone 25 |
|   Line of response (LOR) 27 |
|     Compton cone - LOR intersection 27b |
|   Volume of interest (target zone) 27c |
|   Ray of scintillation light 53 |
|   Major face-coupled detection module 50 |
|     Scintillator array 51 |
|     Photon sensor array 52 |

The invention claimed is:

1. A gamma ray detection system comprising a detection module assembly including at least two detection modules configured for positron emission tomography (PET) scanning of a target zone, each detection module comprising a plurality of stacked monolithic scintillator plates each having a major surface oriented to generally face the target zone and lateral minor surfaces defining edges of the scintillator plates, the major surface having a greater surface area than the surface area of the lateral minor surfaces, and a plurality of photon sensors being mounted against each of said edges configured to detect and determine the position within the plane of the major surface of scintillation events in the scintillator plates from gamma rays incident on the major surfaces, wherein the gamma ray detection system is further configured to function as a Compton camera, at least one scintillator plate that is not the scintillator plate closest to the target zone being configured as an absorber scintillator plate for said Compton camera, wherein photon sensors coupled to at least two radially stacked scintillator plates are connected to processing circuitry configured to apply Compton kinematic rules to determine whether two coincident block events corresponds to a forward or backward-scattered Compton scattering followed by absorption, wherein the processing circuitry is configured to utilize the interaction coordinates of the photoelectric absorption as LOR-endpoint for a forward-Compton scattered gamma ray originating from electron-positron annihilation with a Compton scattering-induced energy deposition below a threshold.

2. The gamma ray detection system according to claim 1, wherein the processing circuitry is configured to reject events appearing to originate from primary gamma rays entering the detector from a radially outward direction.

3. The gamma ray detection system according to claim 1, wherein the processing circuitry is configured to discard Compton scattered events exceeding a configurable, primary gamma ray energy-dependent, scattering angle in order to improve angular resolution.

* * * * *